United States Patent
Berl

(10) Patent No.: US 8,785,665 B2
(45) Date of Patent: Jul. 22, 2014

(54) SURFACTANT-ENABLED TRANSITION METAL-CATALYZED CHEMISTRY

(75) Inventor: Volker Berl, New York, NY (US)

(73) Assignee: Mycell Technologies, LLC, Paramus, NJ (US)

( * ) Notice: Subject to any disclaimer, the term of this patent is extended or adjusted under 35 U.S.C. 154(b) by 433 days.

(21) Appl. No.: 12/958,288

(22) Filed: Dec. 1, 2010

(65) Prior Publication Data

US 2011/0130562 A1 Jun. 2, 2011

Related U.S. Application Data

(60) Provisional application No. 61/265,615, filed on Dec. 1, 2009.

(51) Int. Cl.
   *C07D 311/72* (2006.01)
(52) U.S. Cl.
   USPC ............................................. 549/410
(58) Field of Classification Search
   USPC ........................................... 549/408
   See application file for complete search history.

(56) References Cited

U.S. PATENT DOCUMENTS 6,045,826 A * 4/2000 Borowy-Borowski et al. .............................. 424/451

OTHER PUBLICATIONS

Lipshutz. Organic Letters, vol. 10, No. 7 (2008), pp. 1333-1336.*
Lipshutz. Organic Letters, vol. 10, No. 7 (2008), pp. 1325-1332.*
Smith. AAPS Journal, vol. 5 No. S1 (2003) Available at: http://www.aapsj.org/abstracts/Am_2003/AAPS2003-000558.Pdf.*
Lipshutz, Bruce. Aldrichimica Acta vol. 41, No. 3 (2008) 59-72.*
Maskill, Howard. The investigation of Organic Reactions and Their Mechanisms. Blackwell Publishing. 2006. 63-64.*
Bruce H. Lipshutz and Subir Ghorai, Transition-Metal-Catalyzed Cross-Couplings Going Green: in Water at Room Temperature, Aldrichimica Acta, vol. 41, No. 3, 2008.

* cited by examiner

*Primary Examiner* — Golam M M Shameem
*Assistant Examiner* — Laura Daniel
(74) *Attorney, Agent, or Firm* — Sam L. Nguyen; Hamilton, Desanctis & Cha, LLP

(57) ABSTRACT

In one embodiment, the present application discloses mixtures comprising (a) water in an amount of at least 1% wt/wt of the mixture; (b) a transition metal catalyst; and (c) one or more solubilizing agents; and methods for using such mixtures for performing transition metal mediated bond formation reactions.

15 Claims, 1 Drawing Sheet

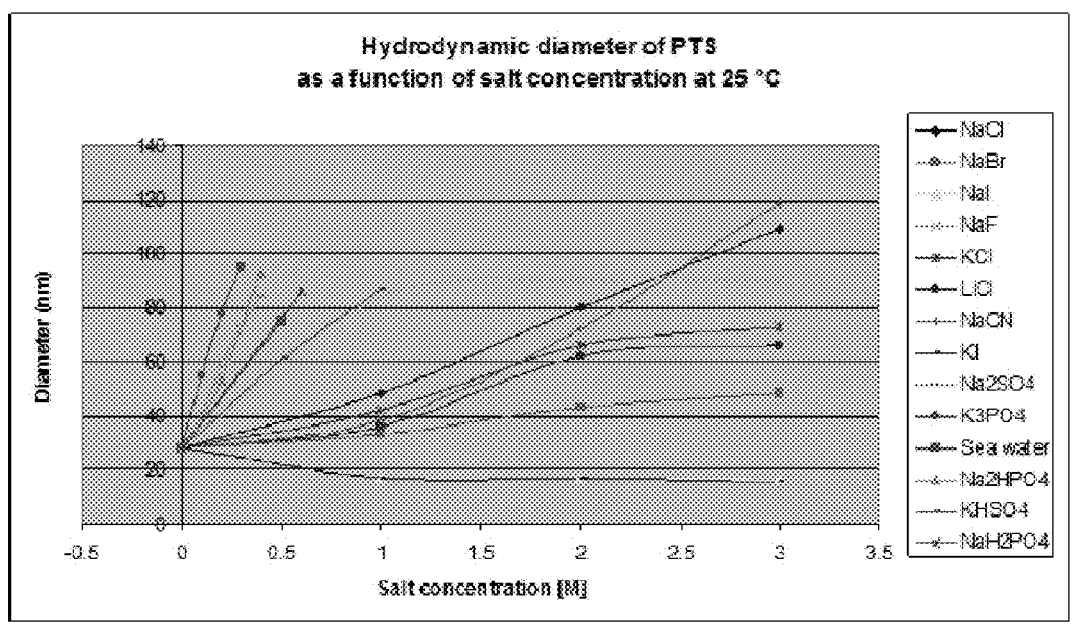

SURFACTANT-ENABLED TRANSITION METAL-CATALYZED CHEMISTRY

RELATED APPLICATION

This application claims the benefit of U.S. Provisional Application No. 61/265,615, filed Dec. 1, 2009, which is incorporated herein by reference.

FIELD OF THE INVENTION

The invention provides compositions and methods for performing a variety of transition metal-catalyzed chemical reactions using a surfactant (or "solubilizing agent") as disclosed herein, and include, for example, surfactants such as tocopherol polyethylene glycol 750-Me succinate (TPGS-M-PEG-750).

BACKGROUND

The TPGS series of surfactants was described by Kodak back in the 1950's (Cawley, et al., U.S. Pat. No. 2,680,749). The use of these succinate-based surfactants in synthetic chemistry in water (such as for "green" chemistry), however, has never been studied. Use of the related surfactant, polyoxyethanyl-tocopheryl sebacate (PTS) is known, and has been studied in a number of aqueous reactions. Lipshutz et al., *Organic Letters,* 2008, 10: 3793-3796; Lipshutz et al., *Organic Letters,* 2008, 10: 1333-1336, Lipshutz et al., *Organic Letters,* 2008, 10: 1329-1332, Lipshutz et al., *Organic* Letters, 2008, 10: 1325-1328; Lipshutz, et al., *Advanced Synthesis & Catalysis,* 2008, 350: 963-956; and Lipshutz, et al., *Organic Letters,* 2008, 10: 5329-5332.

Nevertheless, there remains a need for a surfactant that can be used advantageously in a wide variety of chemistries. In particular, the problem of identifying a surfactant that can be made far more economically, and that generally leads to better reaction efficiencies. The present invention solves these issues, as well as other associated problems.

SUMMARY OF THE INVENTION

In unpublished work, several surfactants have been studied, such as those in the TPGS series, looking for good reaction efficiency in a variety of chemical reactions in water at room temperature (rt). It is far from obvious, given all the possibilities (various PEGs, M-PEGs, and their associated changes in viscosity, dissolution in water, HLB values, and particle sizes), which, if any, would be uniformly as good or better than other surfactants now available commercially. In one embodiment, we have found that TPGS-M-PEG-750, meaning the unsymmetrical diester made from racemic vitamin E, a succinate (4-carbon, dicarboxylic acid) linker, and PEG-750 monomethyl ether (M-PEG-750), appears to uniformly work very well for a broad range of common cross-coupling and metathesis reactions. One particular advantage is that the production of this surfactant is economical, given that the cost of its components, all items of commerce, is low. Furthermore, as a PEG monomethyl ether, TPGS-M-PEG-750 contains only one possible terminus that can react, thereby eliminating options for multiple PEG-related side products. The original Kodak synthesis did not follow along these lines of reasoning; in fact, the original TPGS-1000 is not made with M-PEG-1000. Moreover, the original Kodak synthesis employed natural vitamin E, which is far more expensive than racemic vitamin E, which today is readily available. A third major difference comes in the method of preparation of TPGS-M-PEG-750, in which the efficiency of use of vitamin E (unlike any literature route to date) is extremely high. This improves dramatically both the cost and quality (i.e., impurity profile) of the resulting surfactant.

Use of TPGS-M-PEG-750 in a number of chemical reactions compares very favorably with other approaches, such as using polyoxyethanyl-tocopheryl sebacate (PTS). Here, the yields are as good, or better, while the economics are far more attractive insofar as cost to make the surfactant is concerned. Other commercially available surfactants can, on occasion, give similar and even superior levels of conversion and resulting yields (e.g., Brij catalysts, in particular Brij-30 and Brij-35; see examples; vide infra), and are herein included by reference in this technology, although the generality of these does not match that of TPGS-M-PEG-750. Cross-coupling, metathesis and other industry-valued reactions that take advantage of the compositions and methods of the present invention can be performed under green conditions (i.e., in water at room temperature, without organic solvents, and with no energy consumption due to heating or cooling), which provide considerable social benefits through the preservation of the environment.

Thus, in one aspect, the invention provides a mixture comprising (a) water, (b) a transition metal catalyst and (c) a solubilizing agent having the formula $Y^1\text{-}L^1\text{-}Z$ wherein Z is natural or synthetic alpha-tocopherol, and $Y^1\text{-}L^1\text{-}$ has the formula:

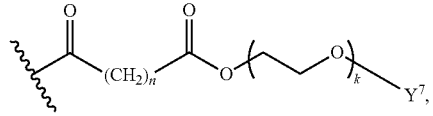

wherein n is an integer selected from 1-14, k is an integer selected from 1-250, and $Y^7$ is selected from H and methyl, with the proviso that if $Y^7$ is H and n is 8, k is not an integer selected from 13-15; and if $Y^7$ is H and n is 2, k is not an integer selected from 21-24. In other embodiments, the surfactant is TPGS-M-PEG-750.

In one aspect, the invention provides a method of performing transition metal-mediated bond formation in an aqueous solvent, the method comprising: contacting a coupling substrate with a mixture of the invention under conditions appropriate to form a bond between a first atom of the coupling substrate and a second atom of a member selected from (i) the coupling substrate and (ii) a coupling partner.

In other embodiments, the bond is formed based on a mechanism selected from olefin cross-metathesis, ring closing metathesis, Sonogashira coupling, Heck coupling, direct amination of free allylic alcohols, amination with allylic ethers, C—H activation (Fujiwara-Moritani reactions and related couplings), Suzuki-Miyaura coupling, C—H activation/arylations/heteroarylations and related couplings, Buchwald-Hartwig amination, organozinc-mediated cross-couplings, borylations of aromatic rings and allylic silylations of allylic ethers.

In another embodiment, there is provided a mixture comprising (a) water in an amount of at least 1% wt/wt of the mixture; (b) a transition metal catalyst; and (c) one or more solubilizing agents selected from the group consisting of solubilizing agents having a hydrophilic-lipophilic balance (HLB) of 8-18, HLB of 7-9, HLB of 8-12 or HLB of 13-15, or a solubilizing agent having the formula $Y^1\text{-}L^1\text{-}Z$ wherein Z is natural or synthetic alpha-tocopherol, or a ubiquinol moiety or a ubiquinol moiety containing a covalently bound catalyst, and $Y^1\text{-}L^1\text{-}$ has the formula:

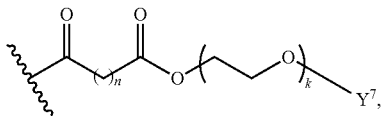

wherein n is an integer selected from 1-14, k is an integer selected from 1-250, and $Y^7$ is selected from H and methyl, or mixtures of solubilizing agents; with the proviso that if $Y^7$ is H and n is 8, k is not an integer from 13-15; and if $Y^7$ is H and n is 2, k is not an integer from 21-24.

In another embodiment, there is provided a method for performing a transition metal mediated bond formation, the method comprising: contacting a coupling substrate with a mixture comprising: (a) water in an amount of at least 1% wt/wt of the mixture; (b) a transition metal catalyst; and (c) one or more solubilizing agents selected from the group consisting of solubilizing agents having a hydrophilic-lipophilic balance (HLB) of 8-18, HLB of 7-9, HLB of 8-12 or HLB of 13-15, or a solubilizing agent having the formula $Y^1\text{-}L^1\text{-}Z$ wherein Z is a natural or synthetic alpha-tocopherol, or a ubiquinol moiety, and $Y^1\text{-}L^1\text{-}$ has the formula:

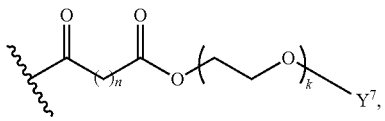

wherein n is an integer selected from 1-14, k is an integer selected from 1-250, and $Y^7$ is selected from H and methyl, or mixtures of solubilizing agents; with the proviso that if $Y^7$ is H and n is 8, k is not an integer from 13-15; and if $Y^7$ is H and n is 2, k is not an integer from 21-24; under conditions appropriate to form a bond between a first atom of the coupling substrate and a second atom of a member selected from (i) the coupling substrate and (ii) a coupling partner. In one aspect of the method, the coupling reaction involving only a single coupling substrate may be an intramolecular bond forming reaction. In another aspect, the transition metal mediated bond formation is performed in an aqueous solvent. In another aspect, the bond is a carbon-carbon, carbon-heteroatom or carbon-hydrogen bond. In another aspect, the coupling substrate is selected from substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl; and wherein the coupling partner is selected from H, substituted or unsubstituted amine, substituted or unsubstituted silane, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. In another aspect, the coupling substrate is a substituted or unsubstituted alkene, a substituted or unsubstituted alkyne, a substituted or unsubstituted enyne, a substituted or unsubstituted enone or enoate or a substituted or unsubstituted ynone or ynoate. In another aspect, the coupling substrate is selected from a substituted or unsubstituted vinyl halide, substituted or unsubstituted vinyl pseudohalide, substituted or unsubstituted allylic alcohol, substituted or unsubstituted allylic ether, substituted or unsubstituted aryl or heteroaryl halide and substituted or unsubstituted aryl or heteroaryl pseudohalide. In another aspect, the coupling partner is selected from a mono-substituted, disubstituted, trisubstituted, or tetrasubstituted alkene, mono-substituted or disubstituted alkyne, substituted or unsubstituted aryl or heteroaryl halide and substituted or unsubstituted aryl or heteroaryl pseudohalide. In another aspect, the bond is formed from a transition metal-catalyzed cross-coupling reactions comprising olefin cross-metathesis, ring closing metathesis, Sonogashira coupling, Heck coupling, direct amination of free allylic alcohols, aminations of allylic ethers, C—H activation reactions (e.g., Fujiwara-Moritani couplings, arylations and heteroarylations of aromatic and heteroaromatic rings, etc.), Suzuki-Miyaura coupling, Buchwald-Hartwig amination, Negishi couplings, benzylic couplings (halides, pseudohalides, etc.) with aryl halides or pseudohalides, silylations of allylic ethers, and all types of aryl-aryl (e.g., combinations of aromatic and heteroaromatic) cross-couplings (biaryl formation). In another aspect, the transition metal mediated bond formation reaction is accelerated by increasing the ionic strength of the reaction medium and/or by the reduction of the pH of the reaction mixture. In another aspect of the method, increasing the ionic strength is performed by the addition of a metal salt or mixtures of salts, and/or the pH is reduced to a range of pH 2-6.

Description of Embodiments

Definitions

Unless defined otherwise, all technical and scientific terms used herein generally have the same meaning as commonly understood by one of ordinary skill in the art to which this invention belongs. The techniques and procedures are generally performed according to conventional methods in the art and various general references, which are provided throughout this document. The nomenclature used herein and the laboratory procedures in analytical chemistry, and organic synthetic described below are those well known and commonly employed in the art. Standard techniques, or modifications thereof, are used for chemical syntheses and chemical analyses.

The term "alkyl," by itself or as part of another substituent, means, unless otherwise stated, a straight or branched chain, or cyclic hydrocarbon radical, or combination thereof, which may be fully saturated, mono- or polyunsaturated and can include mono-, di- and multivalent radicals, having the number of carbon atoms designated (i.e. $C_1$-$C_{20}$ means one to twenty carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl." Alkyl groups that are limited to hydrocarbon groups are termed "homoalkyl."

The term "alkylene" by itself or as part of another substituent means a divalent radical derived from an alkane, as exemplified, but not limited, by —$CH_2CH_2CH_2CH_2$—, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms, for example, ($C_1$-$C_8$)alkyl, ($C_1$-$C_6$)alkyl, ($C_1$-$C_3$)alkyl, etc. . . .

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom selected from the group consisting of O, N, Si, B, Sn, P, F, Cl, Br, I and S, and wherein the nitrogen, phosphorus and sulfur atoms may optionally be oxidized and the nitrogen and phosphorus heteroatom may optionally be quaternized. The heteroatom(s) O, N, B, P, Sn and S and Si may be placed at any interior position of the heteroalkyl group or at the position at which the alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$ and —CH=CH—N($CH_3$)—$CH_3$. Up to three heteroatoms may be consecutive, such as, for example, —$CH_2$—NH—$OCH_3$, —$CH_2$—O—B(OEt)$_2$ and —$CH_2$—O—Si($CH_3$)$_3$. Similarly, the term "heteroalkylene" by itself or as part of another substituent means a divalent radical derived from heteroalkyl, as exemplified, but not limited by, —$CH_2$—$CH_2$—S—$CH_2$—$CH_2$—and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—.

In general, an "acyl substituent" is also selected from the group set forth above. As used herein, the term "acyl substituent" refers to groups attached to, and fulfilling the valence of a carbonyl carbon that is either directly or indirectly attached to a particular group, such as a polycyclic nucleus of the compounds of the present invention.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like. The term "pseudohalides", by themselves or as part of another substituent, unless otherwise stated, refers to species resembling halides in their charge and reactivity. They are generally considered to be a good leaving group in a substitution reaction. Common examples are azides (NNN—), isocyanate (—NCO), isocyanide, (CN—), triflate (—$OSO_2SF_3$) and mesylate ($CH_3SO_2O$—).

The term "aryl" means, unless otherwise stated, a polyunsaturated, aromatic, hydrocarbon substituent which can be a single ring or multiple rings (preferably from 1 to 3 rings) which are fused together or linked covalently. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

The term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") includes both substituted and unsubstituted forms of the indicated radical. Preferred substituents for each type of radical are provided below.

Substituents for alkyl, and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generally referred to as "alkyl substituents" and "heteroakyl substituents," respectively, and they can be one or more of a variety of groups selected from, but not limited to: —OR', =O, =NR', =N—OR', —NR'R", —SR', -halogen, —SiR'R"R'", —OC(O)R', —C(O)R', —$CO_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR"R", —NRSO$_2$R', —CN and —NO$_2$ in a number ranging from zero to (2m'+1), where m' is the total number of carbon atoms in such radical. R', R", R'" and R"" each independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When R' and R" are attached to the same nitrogen atom, they can be combined with the nitrogen atom to form a 3-, 4-, 5-, 6- or 7-membered ring. For example, —NR'R" is meant to include, but not be limited to, 1-aziridine, 1-pyrrolidinyl and 4-morpholinyl. One of skill in the art will understand that the term "alkyl" is meant to include groups including carbon atoms bound to groups other than hydrogen groups, such as haloalkyl (e.g., —$CF_3$ and —$CH_2CF_3$) and acyl (e.g., —$C(O)CH_3$, —$C(O)CF_3$, —$C(O)CH_2OCH_3$, and the like).

Similar to the substituents described for the alkyl radical, the aryl substituents and heteroaryl substituents are generally referred to as "aryl substituents" and "heteroaryl substituents," respectively and are varied and selected from, for example: —OR', =O, =NR', =N—OR', —NR'R", —SR', -halogen, —SiR'R"R''', —OC(O)R', —C(O)R', —$CO_2$R', —CONR'R", —OC(O)NR'R", —NR"C(O)R', —NR'—C(O) NR"R''', —NR"C(O)$_2$R', —NR—C(NR'R")=NR''', —S(O) R', —S(O)$_2$R', —S(O)$_2$NR'R", —NRSO$_2$R', —CN and —$NO_2$, —R', —$N_3$, —CH(Ph)$_2$, fluoro($C_1$-$C_4$)alkoxy, and fluoro($C_1$-$C_4$)alkyl, in a number ranging from zero to the total number of open valences on the aromatic ring system; and where R', R", R''' and R'''' are preferably independently selected from hydrogen, ($C_1$-$C_8$)alkyl and heteroalkyl, unsubstituted aryl and heteroaryl, (unsubstituted aryl)-($C_1$-$C_4$)alkyl, and (unsubstituted aryl)oxy-($C_1$-$C_4$)alkyl. When a compound includes more than one R group, for example, each of the R groups is independently selected as is each R', R", R''' and R'''' group when more than one of these groups are present.

Two of the aryl substituents on adjacent atoms of the aryl or heteroaryl ring may optionally be replaced with a substituent of the formula -T-C(O)—(CRR')$_q$—U—, wherein T and U are independently —NR—, —O—, —CRR'— or a single bond, and q is an integer from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R''')$_d$—, where s and d are independently integers of from 0 to 3, and X is —O—, —NR'—, —S—, —S(O)—, —S(O)$_2$—, or —S(O)$_2$NR'—. The substituents R, R', R" and R''' are preferably independently selected from hydrogen or substituted or unsubstituted ($C_1$-$C_6$)alkyl.

As used herein, the term "heteroatom" includes oxygen (O), nitrogen (N), sulfur (S), phosphorus (P), boron (B), tin (Sn) and silicon (Si).

The term "surfactant," "surface active agent," or "solubilizing agent" (used interchangeably) refers to organic compounds that are amphiphilic, i.e., that contain both hydrophobic groups (their "tails") and hydrophilic groups (their "heads"). Therefore, they are soluble in both organic solvents and water. Exemplary solubilizing agents of use in the invention include vitamin E, as found in, e.g. TPGS (tocopherol propylene glycol succinate, a water-soluble form of vitamin E). As employed herein, the term "surfactant" may include a single surfactant or a mixture (or combination) of two, three or more surfactants.

The term "ynoate" means an unsaturated alkyne that is attached to an ester. Representative ynoates include H—CC—C(O)$_2$R, R'—CC—C(O)$_2$R etc. . . . where R and R' are independently a substituted or unsubstituted ($C_1$-$C_8$) alkyl, substituted or unsubstituted heteroalkyl, substituted or unsubstituted aryl and substituted or unsubstituted heteroaryl or as defined herein.

The term "enyne" means a molecule containing both alkenyl and alkynyl functional groups.

Solubilizing Agents:

Though any 2-component ($Y^1$—Z) surfactant having the desired properties can be used in the methods and mixtures of the invention with varying levels of success, in various embodiments, the present invention makes use of a solubilizing agent having a 3-component structure according to the formula $Y^1$-$L^1$-Z wherein $Y^1$, $L^1$ and Z are as described herein.

In exemplary embodiments, Z is natural or synthetic alpha-tocopherol, and $Y^1$-$L^1$- has the formula:

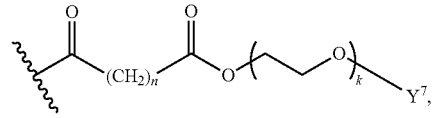

wherein n is an integer selected from 1-14, k is an integer selected from 1-250, and $Y^7$ is selected from H and methyl, with the proviso that if $Y^7$ is H and n is 8, k is not an integer selected from 13-15; and if $Y^7$ is H and n is 2, k is not an integer selected from 21-24.

In some embodiments, $Y^7$ is methyl. In other embodiments, $Y^7$ is methyl, and Z is racemic (unnatural) alpha-tocopherol. In other embodiments, n is an integer selected from 1-8. In other embodiments, n is an integer selected from 1-4. In other embodiments, n is 2. In other embodiments, k is an integer selected from 10-150. In other embodiments, k is an integer selected from 10-50. In other embodiments, k is an integer selected from 16-20. In other embodiments, k is 17.

Z

In one embodiment, Z is selected from a substituted or unsubstituted tocopherol and a substituted or unsubstituted tocotrienol. In another embodiment, Z is an α-, β-, γ-, or Δ-tocopherol. α-(+)-Tocopherol and α-(±)-tocopherol are preferred tocopherols. In another embodiment, Z has a structure according to the following formula:

wherein $R^{20}$, $R^{21}$, $R^{22}$, $R^{23}$, $R^{24}$ and $R^{25}$ are independently selected from hydrogen, halogen, nitro, cyano, $OR^{17}$, $SR^{17}$, $NR^{17}R^{18}$, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl, wherein $R^{17}$ and $R^{18}$ are each independently selected from the group consisting of hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. In another embodiment, $R^{24}$ and/or $R^{25}$ comprises an isoprene moiety.

In some embodiments, Z has a structure according to the following formula:

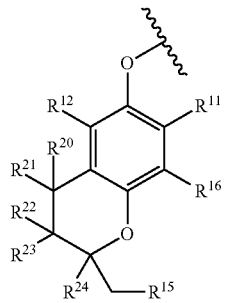

In one embodiment, $R^{15}$ includes a structure which is selected from the following formulas:

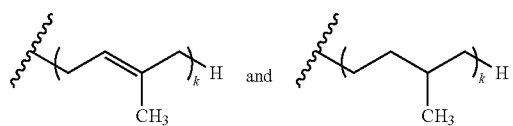

wherein k is an integer selected from 1 to 12. In one embodiment, k is from 2 to 6. In one embodiment, k is 3.

In one embodiment, the solubilizing agent has a structure according to the following formula:

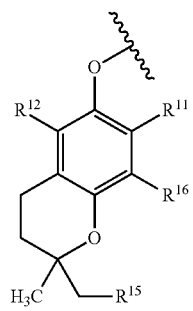

In one embodiment, $R^{11}$, $R^{12}$ and $R^{16}$ are independently selected from H and methyl. In another embodiment, $R^{16}$ is methyl, $R^{11}$ is methyl and $R^{12}$ is methyl. In another embodiment, $R^{16}$ is methyl, $R^{11}$ is H and $R^{12}$ is methyl. In one embodiment, $R^{16}$ is methyl, $R^{11}$ is methyl and $R^{12}$ is H. In another embodiment, $R^{16}$ is methyl, $R^{11}$ is H and $R^{12}$ is H.

$L^1$

In one embodiment, $L^1$ is selected from:

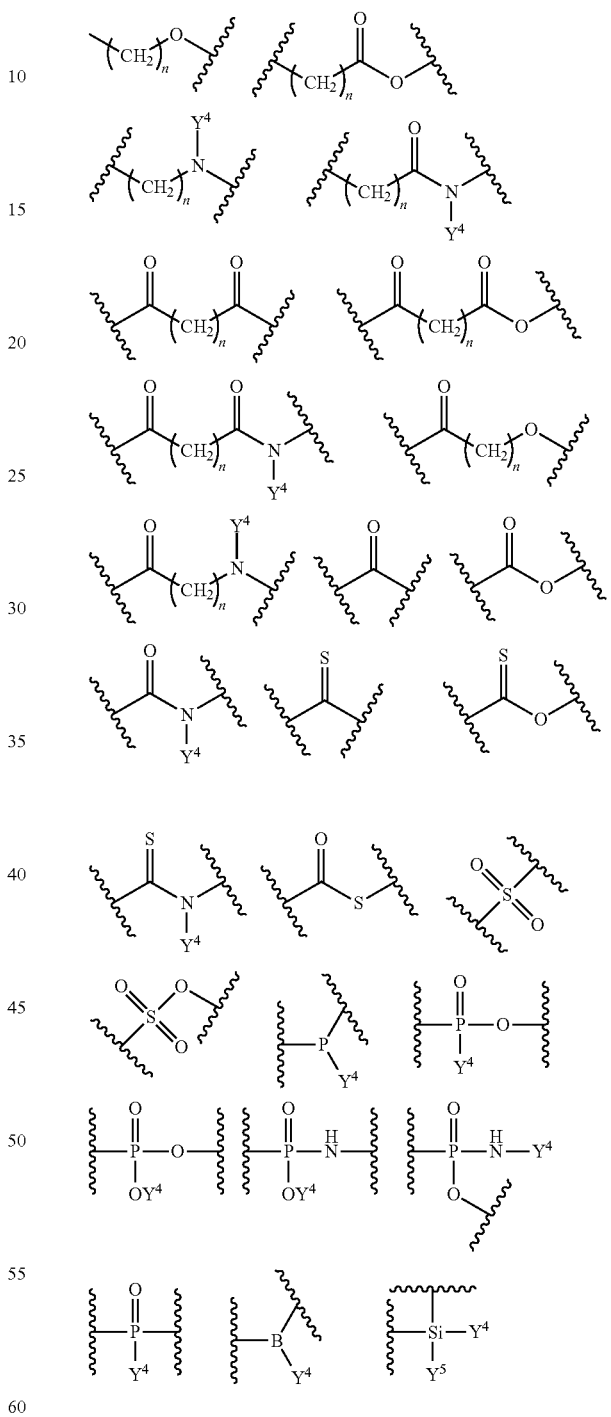

wherein n is an integer selected from 0 to 18. $Y^4$ and $Y^5$ are independently selected from H, substituted or unsubstituted alkyl, substituted or unsubstituted heteroalkyl, substituted or unsubstituted aryl, substituted or unsubstituted heteroaryl and substituted or unsubstituted cycloalkyl and substituted or unsubstituted heterocycloalkyl.

In one embodiment, $L^1$ has a structure of the formula:

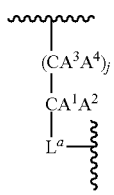

wherein j is an integer selected from 0 to 5000. $A^1$, $A^2$, $A^3$ and $A^4$ are independently selected from H, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, $-NA^5A^6$, $-OA^5$ and $-SiA^5A^6$. $A^5$ and $A^6$ are independently selected from H, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. $L^a$ is a linker.

In certain embodiments, $L^1$ is

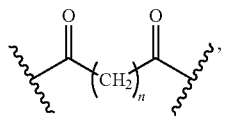

wherein n is an integer selected from 1, 2, 3, 4, 5, 6, 7, 8, 9, 10, 11, 12, 13 and 14. In another embodiment, n is 2.
$Y^1$ In another embodiment, $Y^1$ (depicted herein) is a hydrophilic moiety. The hydrophilic moiety of the solubilizing agent is a hydrophilic molecule having a functional group, which can be used to attach the hydrophilic molecule to Z, either directly or through a linker moiety. Examples of the functional group include esterifiable hydroxy groups, carboxy groups and amino groups. The hydrophilic molecule may be selected from the group consisting of polyalcohols, polyethers, polyanions, polycations, polyphosphoric acids, polyamines, polysaccharides, polyhydroxy compounds, polylysines, and derivatives thereof. Of those, polyethers are preferred, polyalkylene glycols being particularly preferred. The term "polyalkylene glycol" includes polymers of lower alkylene oxides, in particular polymers of ethylene oxide (polyethylene glycols) and propylene oxide (polypropylene glycols), having an esterifiable hydroxy group at least at one end of the polymer molecule, as well as derivatives of such polymers having esterifiable carboxy groups. In one aspect, the residue of the hydrophilic moiety is the entire hydrophilic molecule, except for the atom involved in forming the bond to the substituted or unsubstituted tocopherol and a substituted or unsubstituted tocotrienol moiety or the linker moiety (i.e. an esterified hydroxy group, the oxygen molecule of an ether bond, a carboxy or amino group) or groups, such as terminal hydroxy groups of a polyethylene glycol molecule.

In another aspect, the residue of the hydrophilic moiety is the entire hydrophilic molecule, except for the atom involved in forming the bond to a ubiquinol moiety or the linker moiety (i.e. an esterified hydroxy group, the oxygen molecule of an ether bond, a carboxy or amino group) or groups, such as terminal hydroxy groups of a polyethylene glycol molecule. Accordingly, such residues form a solubilizing agent such as polyoxyethanyl-ubiquinol-sebacate (PQS).

Polyethylene glycols are most particularly preferred for the practice of the present invention. Suitable polyethylene glycols may have a free hydroxy group at each end of the polymer molecule, or may have one hydroxy group etherified with a lower alkyl, e.g., a methyl group. Also suitable are derivatives of polyethylene glycols having esterifiable carboxy groups or amino groups, which may be used to form an amide bond. Polyethylene glycols are commercially available under the trade name PEG, usually as mixtures of oligomers characterized by an average molecular weight. In one embodiment, polyethylene glycol is the solubilizing agent. Polyethylene glycols having an average molecular weight from about 300 to about 5000 are preferred, those having an average molecular weight from about 500 to about 1500, and those having an average molecular weight from about 600 to about 900, and those having an average molecular weight of about 750 being particularly preferred. Both linear and branched PEG molecules can be used as solubilizing agents in the present application. In one embodiment, PEG has between 1 and 250 subunits. In another embodiment, PEG has between 10 and 150 subunits. In another embodiment, PEG has between 10 and 50 subunits. In another embodiment, PEG has between 16 and 20 subunits. In another embodiment, PEG has 17 subunits.

Exemplary poly(ethylene glycol) molecules of use in the invention include, but are not limited to, those having the formula:

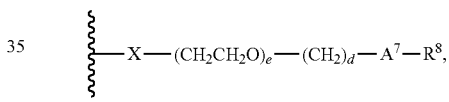

in which $R^8$ is H, OH, $NH_2$, substituted or unsubstituted alkyl, substituted or unsubstituted aryl, substituted or unsubstituted heteroaryl, substituted or unsubstituted heterocycloalkyl, substituted or unsubstituted heteroalkyl, e.g., acetal, OHC—, $H_2N-(CH_2)_q-$, $HS-(CH_2)_q-$, or $-(CH_2)_qC(Y)Z$. "e" represents an integer from 1 to 250. d and q independently represent integers from 0 to 20. Z can represent OH, $NH_2$, leaving groups, e.g., imidazole, p-nitrophenyl, HOBT, tetrazole, halide, $S-R^9$, the alcohol portion of activated esters; $-(CH_2)_pC(Y)V$, or $-(CH_2)_pU(CH_2)_sC(Y)_v$. Y represents H(2), =O, =S, =N—$R^{10}$. X, Y, $Y^1$, $A^7$ and U independently represent the moieties O, S, N—$R^{11}$. V represents OH, $NH_2$, halogen, $S-R^{12}$, the alcohol component of activated esters, the amine component of activated amides, sugar-nucleotides, and proteins. p, q, s and v are integers independently selected from the integers from 0 to 20. $R^9$, $R^{10}$, $R^{11}$ and $R^{12}$ independently represent H, substituted or unsubstituted alkyl, substituted or unsubstituted heteroalkyl, substituted or unsubstituted aryl, substituted or unsubstituted heterocycloalkyl and substituted or unsubstituted heteroaryl.

In a further embodiment the poly(ethylene glycol) is a branched PEG having more than one PEG moiety attached. Examples of branched PEGs are described in U.S. Pat. Nos. 5,932,462; 5,342,940; 5,643,575; 5,919,455; 6,113,906 and 5,183,660; WO/2002/009766; Kodera Y., *Bioconjugate Chemistry*, 1994, 5: 283-288; and Yamasaki et al., *Agric. Biol. Chem.*, 1998, 52: 2125-2127.

In one embodiment, $Y^1$ is the formula

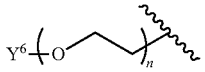

wherein $Y^6$ is selected from $CH_3$ and H, and n is an integer selected from 1 to 250. In another embodiment, n is an integer selected from 10 to 150. In another embodiment, n is an integer selected from 10 to 50. In another embodiment, n is an integer selected from 16 to 20. In another embodiment, n is 17. In another embodiment, $Y^6$ is $CH_3$.

Specific Tocopherols and Linkers

In another embodiment, the solubilizing agent has a structure of Formula IIIa:

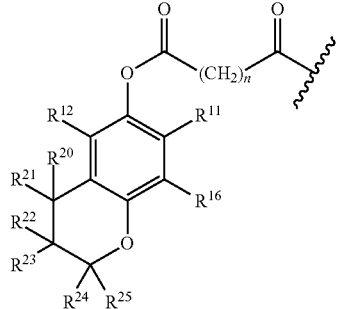

wherein $R^{20}$, $R^{21}$, $R^{22}$, $R^{23}$, $R^{24}$ and $R^{25}$ are selected from halogen, nitro, cyano, $OR^{17}$, $SR^{17}$, $NR^{17}R^{18}$, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl, and n is an integer selected from 1 to 14. In another embodiment, $R^{24}$ and/or $R^{25}$ comprises an isoprene moiety.

In another embodiment, the solubilizing agent is of the Formula IIIa2:

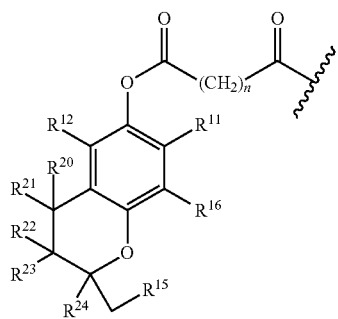

wherein n is a member selected from 1 to 14. In another embodiment, $R^{15}$ includes a structure, which is selected from the following formulas:

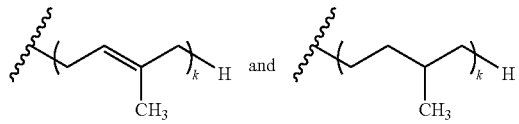

wherein k is an integer selected from 1 to 12. In another embodiment, k is from 2 to 6. In one embodiment, k is 3.

In another embodiment, the solubilizing agent is of the Formula IIIb:

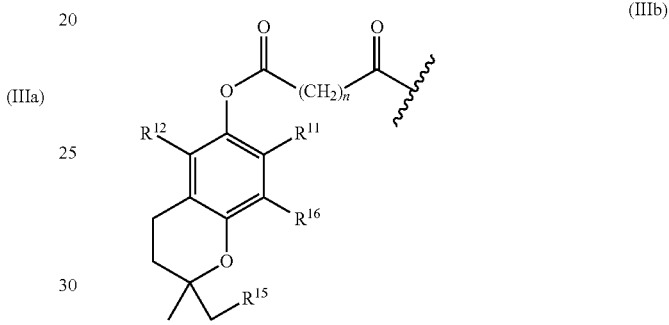

wherein n is selected from 1 to 14 and $R^{11}$, $R^{12}$ and $R^{16}$ are independently selected from H and methyl; and $R^{15}$ is selected from the following formulas:

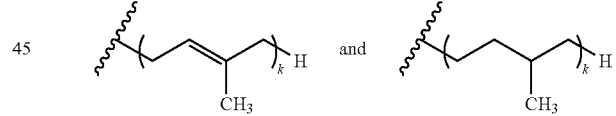

wherein k is an integer selected from 1 to 12. In another embodiment, $R^{16}$ is methyl, $R^{11}$ is methyl and $R^{12}$ is methyl. In another embodiment, $R^{16}$ is methyl, $R^{11}$ is H and $R^{12}$ is methyl. In another embodiment, $R^{16}$ is methyl, $R^{11}$ is methyl and $R^{12}$ is H. In another embodiment, $R^{16}$ is methyl, $R^{11}$ is H and $R^{12}$ is H.

In another embodiment, k is 3, $R^{16}$ is methyl, $R^{11}$ is methyl and $R^{12}$ is methyl. In another embodiment, k is 3, $R^{16}$ is methyl, $R^{11}$ is H and $R^{12}$ is methyl. In another embodiment, k is 3, $R^{16}$ is methyl, $R^{11}$ is methyl and $R^{12}$ is H. In another embodiment, k is 3, $R^{16}$ is methyl, $R^{11}$ is H and $R^{12}$ is H.

In another embodiment, n is 2, k is 3, $R^{16}$ is methyl, $R^{11}$ is methyl and $R^{12}$ is methyl. In another embodiment, n is 2, k is 3, $R^{16}$ is methyl, $R^{11}$ is H and $R^{12}$ is methyl. In another embodiment, n is 2, k is 3, $R^{16}$ is methyl, $R^{11}$ is methyl and $R^{12}$ is H. In another embodiment, n is 2, k is 3, $R^{16}$ is methyl, $R^{11}$ is H and $R^{12}$ is H.

Specific Tocopherols and PEG

In another embodiment, the solubilizing agent is of Formula IIIc:

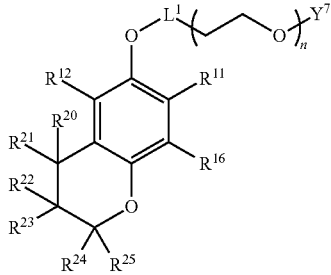

(IIIc)

wherein $R^{20}$, $R^{21}$, $R^{22}$, $R^{23}$, $R^{24}$ and $R^{25}$ are selected from halogen, nitro, cyano, $OR^{17}$, $SR^{17}$, $NR^{17}R^{18}$, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl, and n is an integer selected from 16 to 20, $L^1$ is a linker moiety, $Y^7$ is selected from H and methyl. In an embodiment, $R^{24}$ and/or $R^{25}$ comprises an isoprene moiety.

In another embodiment, the solubilizing agent is of the Formula IIIc2:

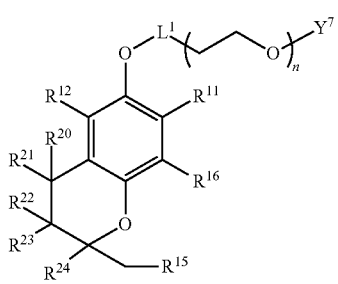

(IIIc2)

wherein n is selected from 16 to 20, $L^1$ is a linker moiety, $Y^7$ is selected from H and methyl. In another embodiment, $R^{15}$ is selected from the formulas:

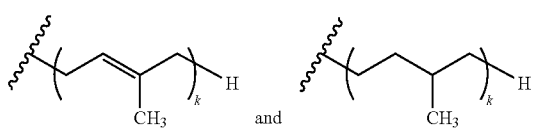

wherein k is an integer selected from 1 to 12. In another embodiment, k is from 2 to 6. In another embodiment, k is 3.

In another embodiment, the solubilizing agent is of the Formula IIId:

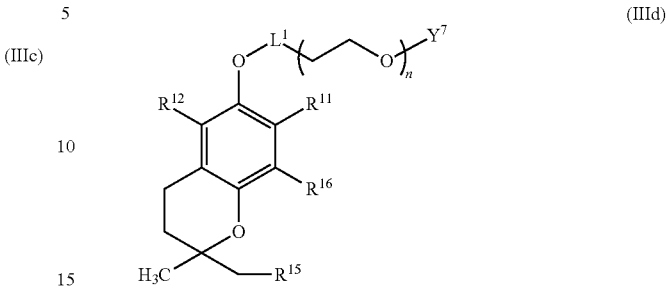

(IIId)

wherein n is an integer selected from 16 to 20 and $R^{11}$, $R^{12}$ and $R^{16}$ are independently selected from H and methyl; and $R^{15}$ is selected from the formulas:

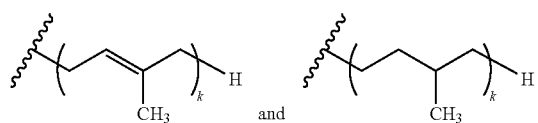

wherein k is an integer selected from 1 to 12. In another embodiment, $R^{16}$ is methyl, $R^{11}$ is methyl and $R^{12}$ is methyl. In another embodiment, $R^{16}$ is methyl, $R^{11}$ is H and $R^{12}$ is methyl. In another embodiment, $R^{16}$ is methyl, $R^{11}$ is methyl and $R^{12}$ is H. In another embodiment, $R^{16}$ is methyl, $R^{11}$ is H and $R^{12}$ is H.

In another embodiment, k is 3, $R^{16}$ is methyl, $R^{11}$ is methyl and $R^{12}$ is methyl. In another embodiment, k is 3, $R^{16}$ is methyl, $R^{11}$ is H and $R^{12}$ is methyl. In another embodiment, k is 3, $R^{16}$ is methyl, $R^{11}$ is methyl and $R^{12}$ is H. In another embodiment, k is 3, $R^{16}$ is methyl, $R^{11}$ is H and $R^{12}$ is H.

Specific Ubiquinol Moiety:

In one embodiment, the solubilizing agent is of the Formula IIIe:

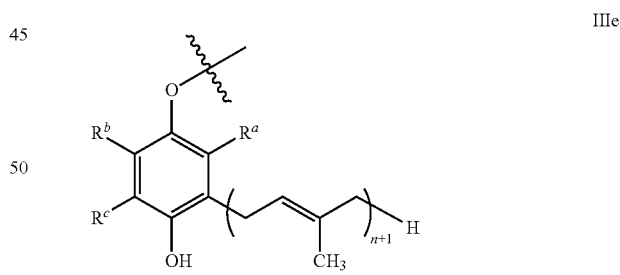

IIIe wherein the n is selected from 1 to 13. $R^a$, $R^b$ and R are independently selected from H, substituted or unsubstituted alkyl and substituted or unsubstituted alkoxy. $R^b$ and $R^c$, together with the carbon atoms to which they are attached, are optionally joined to form a 5- to 7-membered ring. In one embodiment, n is 9. In another embodiment, $R^a$ is methyl. In yet another embodiment, $R^a$ is methyl and $R^b$ and $R^c$ are both methoxy.

In one embodiment, the surfactants or solubilizing agents that may be employed may be selected from solubilizing agents having a hydrophilic-lipophilic balance (HLB) of 8-18, HLB of 7-9 and HLB of 8-12, HLB of 13-15, polyoxyethanyl-tocopheryl-sebacate (PTS), polyoxyethanyl-sitosterol-sebacate (PSS), polyoxyethanyl-cholesterol-sebacate (PCS), polyoxyethanyl-ubiquinol-sebacate (PQS) and combinations or mixtures thereof. In one aspect, the above solubilizing agent is selected from the group consisting of Poloxamer 188, Polysorbate 80, Polysorbate 20, Vit E-TPGS, Solutol HS 15, PEG-40 Hydrogenated castor oil (Cremophor RH40), PEG-35 Castor oil (Cremophor EL), PEG-8-glyceryl capylate/caprate (Labrasol), PEG-32-glyceryl laurate (Gelucire 44/14), PEG-32-glyceryl palmitostearate (Gelucire 50/13); Polysorbate 85, Polyglyceryl-6-dioleate (Caprol MPGO), Mixtures of high and low HLB emulsifiers; Sorbitan monooleate (Span 80), Capmul MCM, Maisine 35-1, Glyceryl monooleate, Glyceryl monolinoleate, PEG-6-glyceryl oleate (Labrafil M 1944 CS), PEG-6-glyceryl linoleate (Labrafil M 2125 CS), Oleic acid, Linoleic acid, Propylene glycol monocaprylate (e.g. Capmul PG-8 or Capryol 90), Propylene glycol monolaurate (e.g., Capmul PG-12 or Lauroglycol 90), Polyglyceryl-3 dioleate (Plurol Oleique CC497), Polyglyceryl-3 diisostearate (Plurol Diisostearique) and Lecithin with and without bile salts, or combinations thereof.

In one embodiment, polyoxyethanyl-ubiquinol-sebacate (PQS) may be prepared where a ubiquinol is used in place of a-tocopherol, where either of the free OH groups in this hydroquinone is attached to a linker via esterification. See Lipshutz, Ghorai, *Organic Letters* 2009, 11, 705.

Using the remaining phenolic OH moiety, a variety of species (e.g., catalysts, pharmaceuticals, nutraceuticals, etc.) can be covalently attached at this site. As a representative example, a catalyst that effects olefin metathesis has been attached to form a new, water-soluble, micellar species that catalyzes the desired metathesis reactions in water at room temperature. In one aspect, this species is both the surfactant and (Grubbs-Hoveyda-1) catalyst combined. The catalyst remains in the aqueous phase, and can be recycled without removal from the reaction vessel.

As with surfactants in the corresponding vitamin E series, the synthesis of PQS relies on a 10-carbon linker diacid. Replacement of sebacic acid with the 4-carbon analog (succinic acid) forms a PQS-modified surfactant.

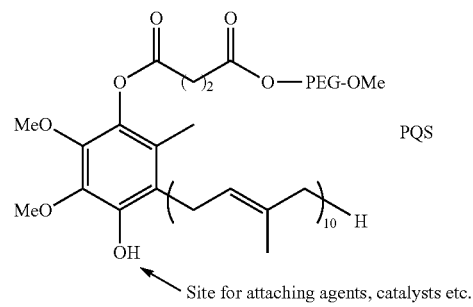

The new form of PQS, derivatized to include the Grubbs-Hoveyda-1 ruthenium carbene catalyst, has been shown to function equally as well as the literature version.

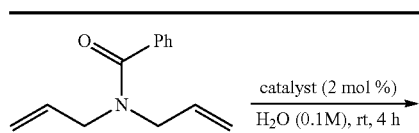

| catalyst | Yield [%] |
|---|---|
| PQS-Grubbs-1 (original) | 94 |
| PQS-Grubbs-1 (new) | 96 |

TPGS-750-M: A Second-Generation Amphiphile for Metal-Catalyzed Cross-Couplings in Water at Room Temperature

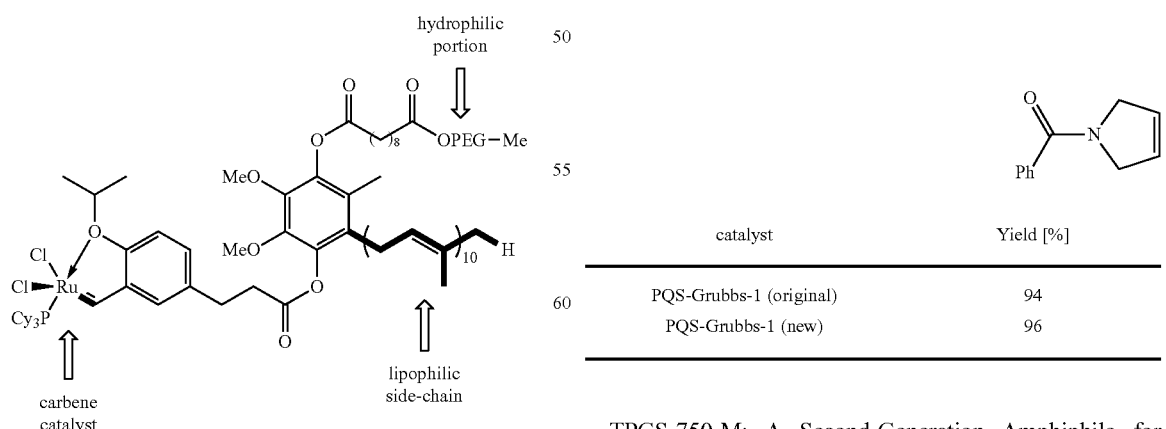

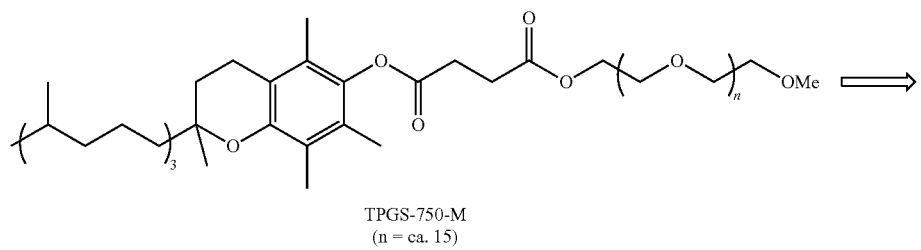

TPGS-750-M
(n = ca. 15)

enables reactions in water @ RT

Heck, Suzuki-Miyaura, aminations, borylations, silylations, Negishi-like olefin metathesis reactions Representative substrates, reagents, catalysts and surfactant enabled transition metal catalyzed reactions, some of which are exemplified using PTS or PQS, are provided below. However, one or more of the above cited surfactants may be employed in the metal catalyzed reactions.

In one embodiment, the reaction may employ one or a mixture of two or surfactants (e.g., TPGS-750-M+PQS bearing a covalently linked catalyst). In one aspect, the ratio of two or more mixture of the surfactants may be about 1:1 to about 5,000:1 (w/w). In another embodiment, the ratio of a mixture of two surfactants may be about 1:1 to about 5,000:1 (w/w), about 1,000:1, about 500:1, about 250:1, about 100:1, about 75:1, about 50:1, about 25:1, about 10:1, about 5:1, about 3:1, about 2:1, or about 1:1. Similarly, for a mixture of three or more surfactants, the ratio may be 1:1:1 to 5,000:1:1 (w/w/w), etc. . . . in the ranges as noted for the two surfactant examples above.

Transition Metal Catalysts

There are many (achiral or nonracemically) ligated transition metal catalysts, or their precursors, of the same or varying oxidation states that are available commercially or by synthesis. Among the most common are Pd catalysts, of both Pd(0) and Pd(II) oxidation states. These have been found to catalyze many "name reactions" (e.g., see [0010]) to which this chemistry in water is especially applicable. Examples of catalysts include PEPPSI, (t-Bu$_2$PPh)$_2$PdCl$_2$, and (Amphos)$_2$PdCl$_2$ among many others Likewise, ruthenium catalysts are particularly useful in synthesis (e.g., for hydrogenation). Among the most commonly used are ruthenium carbene catalysts (e.g., Grubbs, and Grubbs-Hoveyda catalysts) that effect olefin metathesis chemistry.

In certain embodiments, the transition metal catalyst is selected from an organo-palladium or -nickel reagent, organo-copper or -gold reagent, organo-rhodium or -iridium complex, or an organoruthenium reagent, wherein the catalyst is capable of promoting cross-coupling reactions that form a carbon-carbon, carbon-heteroatom or carbon-hydrogen bond. In another aspect, the catalyst promotes cross-coupling reactions that form a carbon-carbon, carbon-heteroatom or carbon-hydrogen bond. Representative types of catalysts that may be employed in the present application are provided below:

Materia:

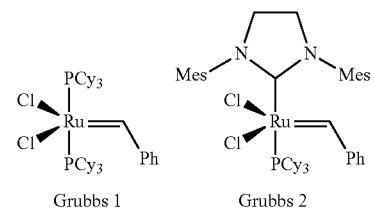

Grubbs 1      Grubbs 2

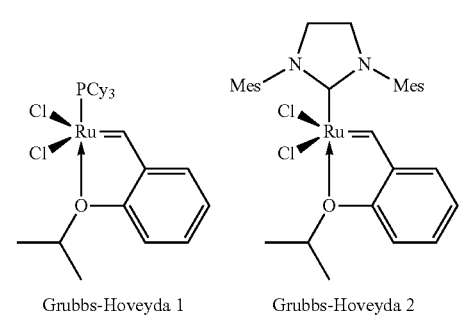

Grubbs-Hoveyda 1      Grubbs-Hoveyda 2

Zannan Pharma Ltd:

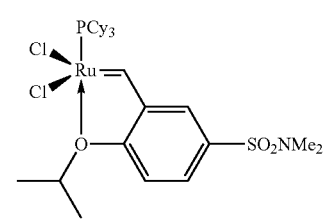

RC-304

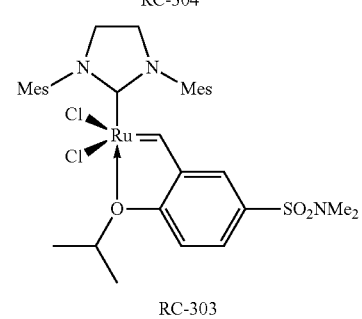

RC-303

Umicore:

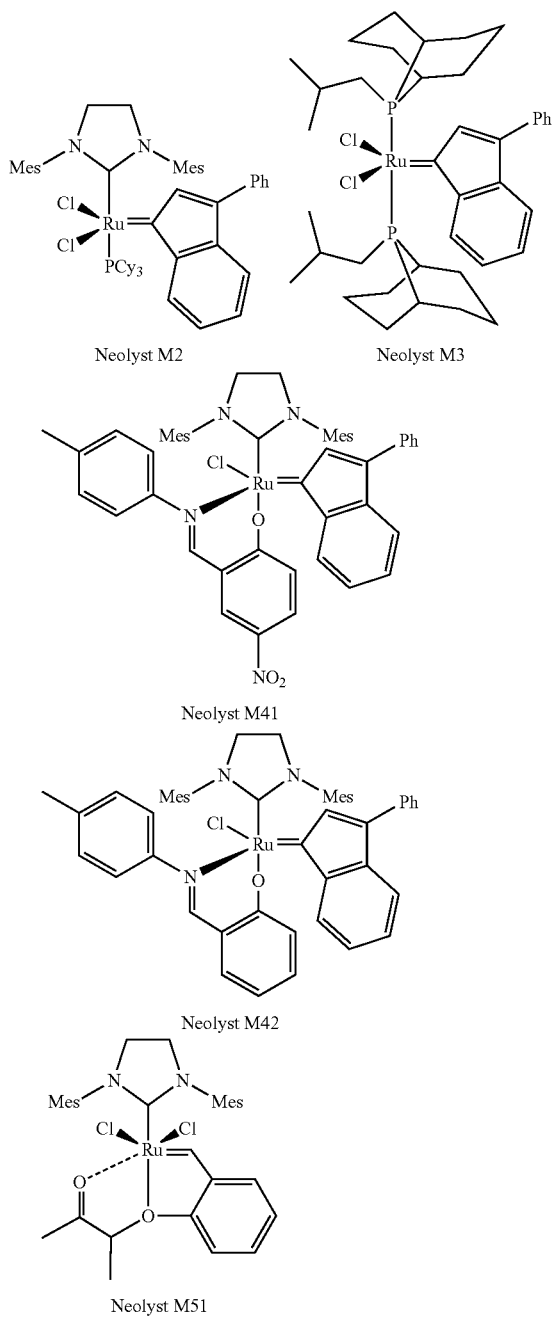

Neolyst M2

Neolyst M3

Neolyst M41

Neolyst M42

Neolyst M51

The Substrates:

Halides: Non-exclusive halides that may be employed as substrates include alkyl, aryl, heteroaryl and vinylic halides; and alkyl, aryl, heteroaryl and vinylic pseudohalides are viable substrates. Numerous functional groups may be present within these reaction partners (e.g., esters, aldehydes, ketones, etc.). In various embodiments, vinyl halides of E or Z composition can be used with maintenance of stereointegrity in the present Pd-catalyzed cross-couplings. Exemplary alkyl halides include, but are not limited to, primary, secondary, or tertiary iodides or bromides, or related pseudohalides (e.g., triflates or other sulfonates).

Unsaturated Systems: Unsaturated carbonyl substrates that may be employed in the reactions may include, e.g., enones and enoates. Other Michael type acceptors include nitro-substituted alkenes, unsaturated, conjugated sulfoxides and sulfones, and unsaturated phosphonates and phosphine oxides. Other unsaturated educts include enynes, dienes and diynes, etc. . . .

Solvents:

In one embodiment, the mixtures or the mixtures of the reactions of the present application comprise water in an amount of at least 1% wt/wt of the mixtures. In another embodiment, the water in the mixture is present in an amount of at least 5%, at least 10%, at least 50%, at least 75%, at least 90% or at least 99% wt/wt or more of the mixture. In another aspect, water is the only solvent medium in the mixture. In one embodiment, the amount of water present in the mixture is sufficient to allow the formation of nanomicelles. In mixtures wherein water is not the only solvent present, one or more suitable non-aqueous solvent or solvent mixtures may be used with water. In one aspect, the solvent or solvent mixture may be a water miscible or partially miscible solvent. In another aspect, non-exclusive examples of the non-aqueous solvent may include $C_1$-$C_6$ alcohols such as methanol, ethanol, propanol, isopropanol, butanol(s), n-butanol, etc. . . . , acetone, ethyl acetate, methyl acetate, THF, acetonitrile, formic acid, acetic acid, ethyleneglycol or PEGs, dioxane, MIBK, MEK, DMSO, DMF, DMA, NMP or mixtures thereof.

Reactions

Many reactions known in the art can be performed under the green conditions disclosed herein. In one aspect, the application provides a method of performing transition metal mediated bond formation in water as the only medium, the method comprising: contacting a coupling substrate with the mixture of any preceding claim under conditions appropriate to form a bond between a first atom of the coupling substrate and a second atom of a member selected from (i) the coupling substrate and (ii) a coupling partner.

Metal or Organometallic Catalysts:

Non-exclusive examples for the different types of metals or metal complexes that may be used to perform different types or classes of reactions include: Boron for performing borylation reactions, for forming carbon-boron bonds; Palladium for performing cross-coupling reactions, oxidations, C—H activation, allylic substitution reactions; Ruthenium for performing olefin metathesis, hydrogenation and transfer hydrogenation, isomerization; Copper for performing click chemistry, (asymmetric) conjugate addition, carbene chemistry, (asymmetric) allylic substitution; Rhodium for performing conjugate addition, cycloisomerization and cyclotrimerization, and asymmetric hydrogenation; Nickel for performing cross coupling reactions, carbometalation, dimerization and polymerization; Iridium for performing hydrogenation, hydroamination and C—H borylation; Gold for performing cyclizations of polyunsaturated compounds, oxidation, nucleophilic addition and Friedel-Crafts Reactions. The catalysts employed may include commercially available catalysts, catalysts that may be prepared in situ, or precursors of catalysts that are related or made from the precursors that form the same or related metal catalysts in one or more different oxidation states (e.g., Pd(0) as the in situ generated active species from a Pd(II) complex).

Representative commercially available Palladium catalysts having different oxidation states that may be employed, include: Pd(O)catalysts: $Pd(PPh_3)_4$, $Pd(P(t\text{-}Bu)_3)_2$, $Pd(dba)_2$, $Pd_2(dba)_3$ and $Pd(PCy_3)_2$; Pd(I) catalysts: $Pd_2Br_2(P(t\text{-}Bu)_3)_2$; Pd(II) catalysts: $Pd(PPh_3)_2Br_2$, $PdCl_2(dtbpf)$, $PdCl_2(Amphos)_2$ and $Pd(CH_3CN)_4(BF_4)_2$; Pd(IV) catalysts: $(NH_4)_2PdCl_6$, $Na_2PdCl_6$ and $K_2PdCl_6$.

In addition, catalysts that may used in the present application include catalysts that may be prepared immediately before use, i.e., prepared by combining individual ingredients (e.g., $PdCl_2+Ph_3P$), and catalysts generated in situ or in the reaction (e.g., a Pd(II) species in the presence of a reducing agent to give a Pd(0) species).

In one embodiment, the bond is a carbon-carbon, carbon-heteroatom or carbon-hydrogen bond. In one embodiment, the coupling substrate is selected from substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl; and wherein the coupling partner is selected from H, substituted or unsubstituted amine, substituted or unsubstituted silane, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. In one embodiment, the coupling substrate is a substituted or unsubstituted alkene.

In one embodiment, the coupling substrate is selected from substituted or unsubstituted vinyl halide, substituted or unsubstituted vinyl pseudohalide, substituted or unsubstituted allylic alcohol and substituted or unsubstituted allylic ether. In one embodiment, the coupling substrate is selected from substituted or unsubstituted aryl or heteroaryl halide and substituted or unsubstituted aryl or heteroaryl pseudohalide.

In one embodiment, the coupling partner is selected from a mono-substituted, disubstituted, trisubstituted or tetrasubstituted alkene, mono-substituted or disubstituted alkyne, substituted or unsubstituted aryl or heteroaryl halide and substituted or unsubstituted aryl or heteroaryl pseudohalide.

In one embodiment, the bond is formed based on processes or mechanisms selected from olefin cross-metathesis including olefin-olefin metathesis, olefin-alkyne metathesis, ring closing metathesis, Sonogashira coupling, Heck coupling, asymmetric Heck reactions, direct amination of free allylic alcohols, amination of allylic ethers, C—H activation reactions (e.g., Fujiwara-Moritani coupling, arylations, etc.), Suzuki-Miyaura coupling, Buchwald-Hartwig aminations, organozinc-mediated cross-couplings, benzylic couplings (halides, pseudohalides, etc.) with aryl halides or pseudohalides, silylations of allylic ethers, borylation reactions (C—H activation, formation of C—B bonds, with sp$^3$ and sp$^2$ carbons and substrates such as aryl halides, alkenyl halides etc. . . . ), copper and ligated copper complexes (copper hydrides), symmetric and asymmetric 1,4-additions to enones and enoates, and all types of aryl-aryl (e.g., aryl-heteroaryl) cross-couplings (biaryl formations).

Acceleration of Surfactant-Enabled Transition Metal-Catalyzed Reactions:

In one embodiment, the reaction rate for the transition metal-catalyzed reactions may be accelerated by changing the ionic strength of the aqueous reaction medium, without increasing the reaction temperature. In one aspect, increasing the ionic strength, such as by the addition of a single salt or a mixture of salts, increases the rate of the reaction. In one aspect, the reaction rate is increased by at least 10%, at least 20%, at least 30%, at least 50%, at least 75%, at least 100% or more. In another aspect, the reaction rate is increased by at least 150%, at least 200%, at least 300% or at least 500% or more. In one variation, the salt is LiF, LiCl, LiI, LiBr, NaF, NaCl, NaBr, NaI, KCl, KBr, KI, NaCN or a combination thereof. In one variation, the salt is in the form of sea water. In another aspect, the salt (single salt or a mixture of salts) concentration in the reaction mixture is about 0.01 M to about 5 M, about 0.1 to about 0.5 M, about 0.1 to about 1.0 M, about 0.1 to about 1.5 M, about 0.1 to about 2.0 M, about o.1 to about 2.5 M, about 0.1 to about 3.0 M, or about 0.1 to about 5.0 M. In another aspect, the salt concentration in the reaction mixture is about 0.2 to about 0.5 M, about 0.3 to about 0.5 M or about 0.3 to about 1.0 M.

In another embodiment, the reaction rate for the transition metal-catalyzed reactions may be accelerated by changing the pH of the aqueous solution without increasing the reaction temperature. In one aspect, the reaction rate may be accelerated by reducing the pH of the solution by adding a salt or a buffer. The pH of the reaction may be lowered to about pH 2-7, about pH 2-6, about pH 2-5, about pH 3-4, or about pH 3-5. The pH of the reaction may be lowered to a pH wherein the substrate, reactants, surfactant(s) and/or the metal complex are not altered, e.g. by hydrolysis or decomposed. In one aspect, the pH of the solution may be lowered by using a standard buffer solution known in the art, at a selected pH, as noted above. In one aspect, the pH of the solution may be lowered by the addition of one or more salts selected from $KHSO_4$, $Na_2SO_4$, $Na_2HPO_4$ or $K_3PO_4$ or mixtures thereof.

In another aspect, the reaction rate for the transition metal-catalyzed reactions may be accelerated by the addition of the above salt or combinations of salt in conjunction with reducing the pH of the reaction mixture.

BRIEF DESCRIPTION OF THE DRAWING

FIGURE: The graph below relates to the effects of salts and salt concentration on the particle size of the solubilizing agent.

Non-exclusive, representative type of reactions, catalysts, substrates and reaction conditions that may be performed using the compositions and methods of the present application include:

Cross-Couplings of Alkyl with Heteroaromatic Halides, in Water at Room Temperature.

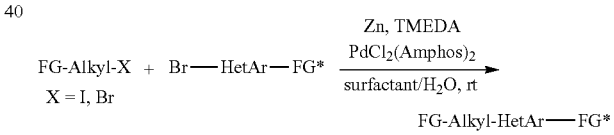

Modified Routes to the "Designer" Surfactant PQS
Stereoselective Negishi-like Couplings of Alkenyl Halides with Alkyl Halides:

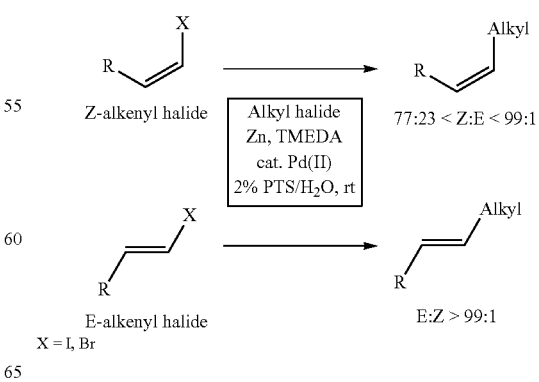

Miyaura Borylations of Aryl Bromides:

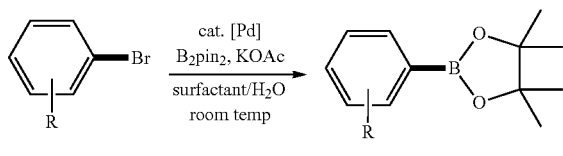

Huang, S.; Voigtritter, K.; Unger, J. B.; Lipshutz, B. H., Asymmetric CuH-Catalyzed 1,4-Reductions in Water @ RT, *Synlett (invited)*, 2010, 2041.

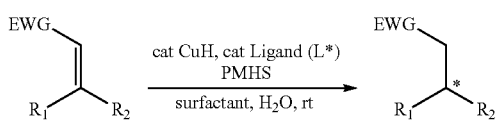

Nishikata, T.; Abela, A. R.; Lipshutz, B. H., Room Temperature C—H Activation & Cross-Coupling of Aryl Ureas in Water, *Angew. Chem. Int. Ed.* 2010, 49, 781.

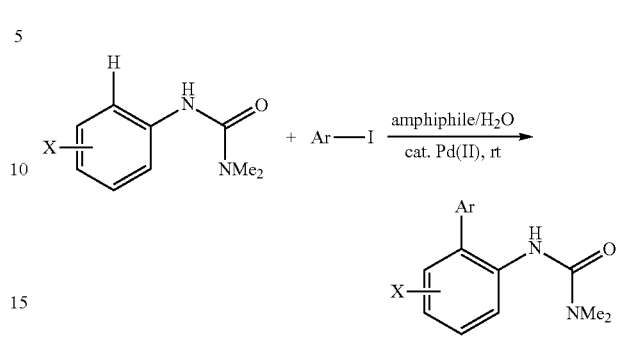

Lipshutz, B. H.; Ghorai, S., PQS-2. Ring-closing and cross-metathesis reactions on lipophilic substrates: in water only at room temperature, with in-flask catalyst recycling, *Tetrahedron S-i-P,* 2010, 66, 1057.

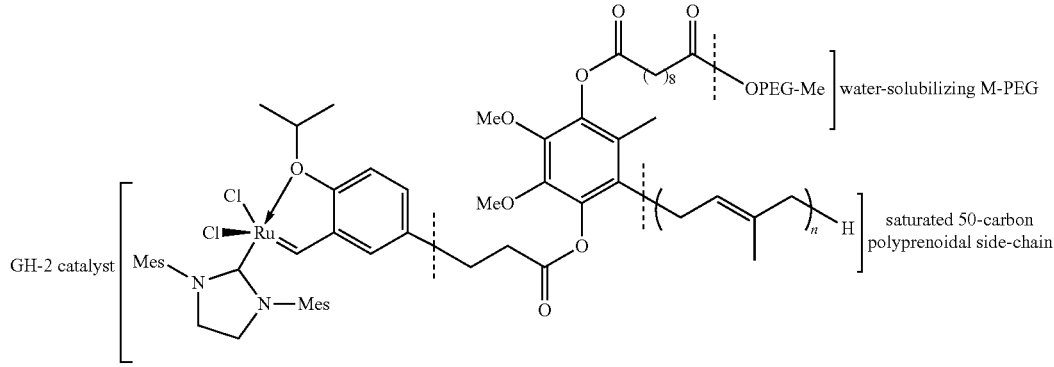

The catalysts employed in the present application may be used in various reactions, including Click chemistry, cross reactions and metathesis, ring-closing metathesis, CuH reduction, Negishi reaction, C—H activation, Fujiwara reactions, borylations, Suzuki-Miyaura reaction, allylic silylation, allylic amination, Buchwald-Hartwig reactions, Songashira reactions and Heck reactions. See Moser, R.; Huang, S.; Abela, A.; Lipshutz, B. H., Sustainability. Getting Organic Solvents Out of Organic Reactions, *Chemistry Today,* 2010, 28, 50.

Nishikata, T.; Lipshutz, B. H., Cationic Pd(II)-Catalyzed Fujiwara-Moritani Reactions at Room Temperature in Water, *Organic Lett.* 2010, 12, 1972.

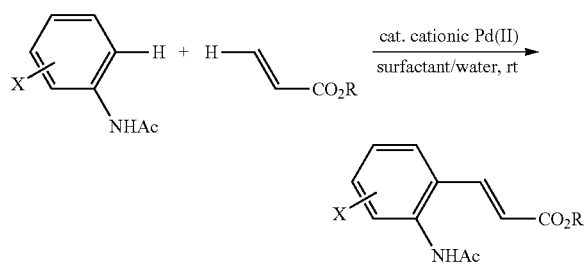

Moser, R.; Nishikata, T.; Lipshutz, B. H., Pd-Catalyzed Synthesis of Allylic Silanes from Allylic Ethers, *Org. Lett.* 2010, 12, 28.

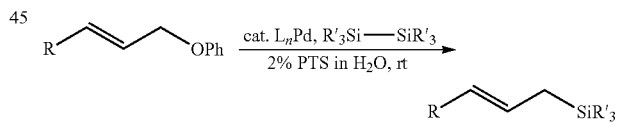

Aminations of Allylic Phenyl Ethers via Micellar Catalysis at Room Temperature in Water, T. Nishikata, B. H. Lipshutz, *Chem. Commun.* 2009, 6472.

Zinc-Mediated, Pd-Catalyzed Cross-Couplings in Water at Room Temperature without Prior Formation of Organozinc Reagents," A. Krasovskiy, C. Duplais, B. H. Lipshutz, *J. Am. Chem. Soc.,* 2009, 131, 15592.

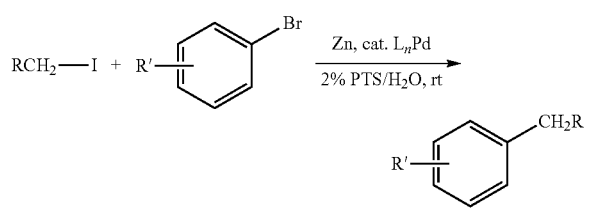

Allylic Ethers as Educts for Suzuki-Miyaura Couplings in Water at Room Temperature, T. Nishikata, B. H. Lipshutz, *J. Am. Chem. Soc.*, 2009, 131, 12103.

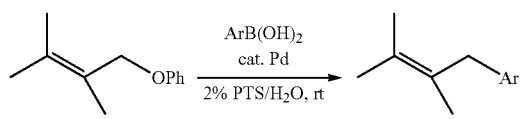

Aminations of Aryl Bromides in Water at Room Temperature, B. H. Lipshutz, D. W. Chung, B. Rich, *Adv. Syn. Catal.* 2009, 351, 1717.

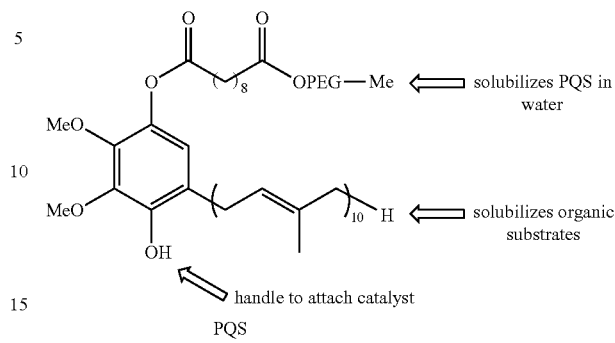

Micellar Catalysis of Suzuki-Miyaura Cross-Couplings with Heteroaromatics in Water, B. H. Lipshutz, A. R. Abela, *Org. Lett.* 2008, 10, 5329.

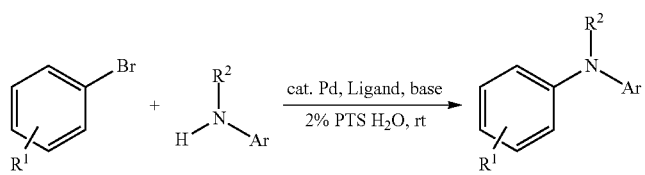

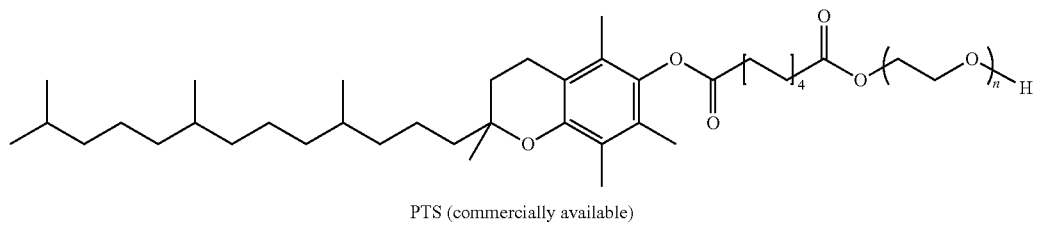

PTS (commercially available)

Amination of Allylic Alcohols in Water at Room Temperature, T. Nishikata, B. H. Lipshutz, *Org. Lett.*, 2009, 11, 2377.

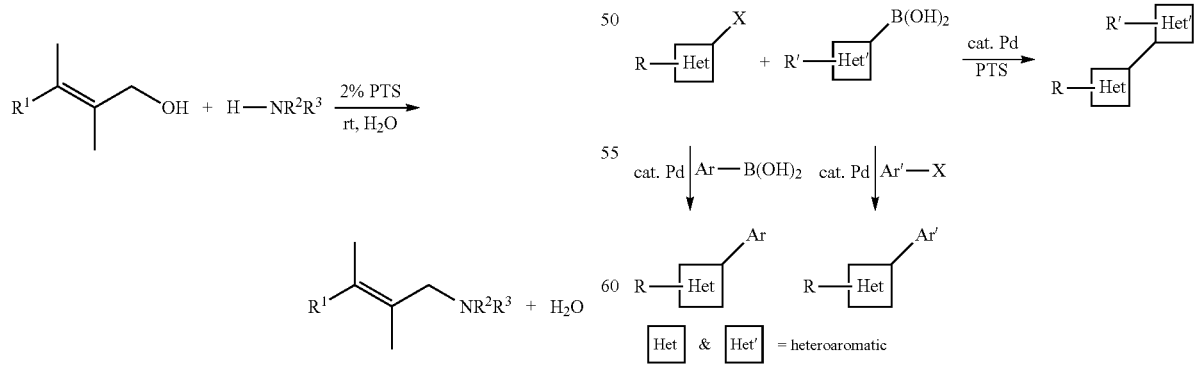

PQS: A Newly Designed Platform for Micellar Catalysis. RCM Reactions, B. H. Lipshutz, S. Ghorai, *Org. Lett.* 2009, 11, 705.

Sonogashira Couplings of Aryl Bromides: Room Temperature, Water Only, No Copper, B. H. Lipshutz, D. W. Chung, B. Rich, *Org. Lett.* 2008, 10, 3793.

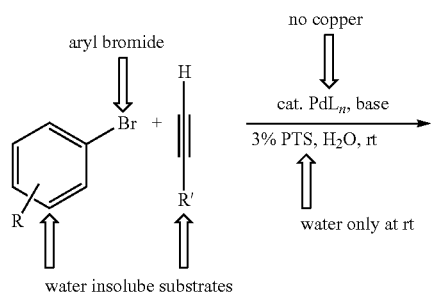

water insoluble substrates 76-99%

Tandem olefin metathesis-elimination reactions. A new route to doubly unsaturated carbonyl derivatives, B. H. Lipshutz, S. Ghorai, Z. V. Boskovic, *Tetrahedron* (invited) 2008, 64, 6949.

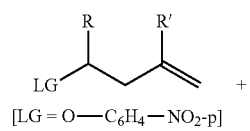

Ring-Closing Metathesis at Room Temperature within Nanometer Micelles Using Water as the Only Solvent, B. H. Lipshutz, S. Ghorai, G. Aguinaldo, *Adv. Syn. Catal.* 2008, 350, 953.

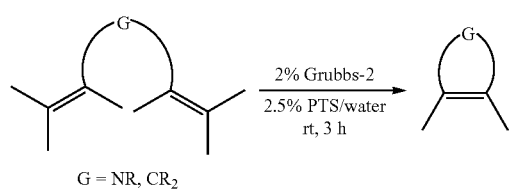

G = NR, CR$_2$

-continued

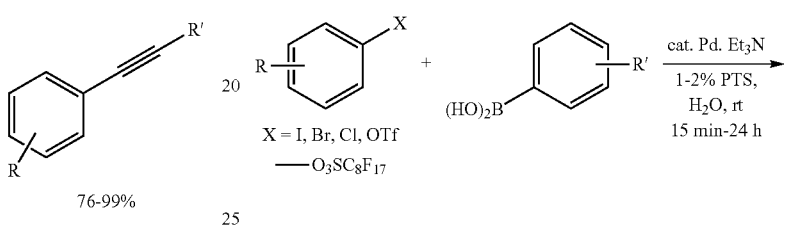

Grubbs-2 catalyst

Room Temperature Suzuki-Miyaura Couplings in Water Facilitated by Nonionic Amphiphiles, B. H. Lipshutz, T. B. Petersen, A. Abela, *Org. Lett.* 2008, 10, 1333.

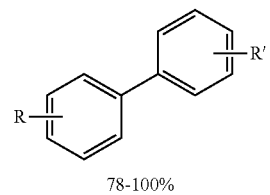

78-100%

Heck Couplings at Room Temperature in Nanometer Aqueous Micelles", B. H. Lipshutz, B. R. Taft, *Org. Lett.* 2008, 10, 1329.

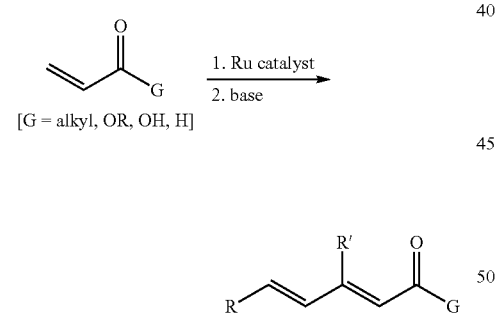

E/Z. 9:1
yields 80-98%
R' = CO$_2$R, aryl

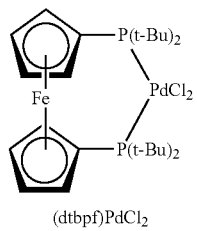

(dtbpf)PdCl$_2$

Olefin Cross-Metathesis Reactions at Room Temperature: B. H. Lipshutz, G. Aguinaldo, S. Ghorai, K. Voigtritter, *Org. Lett.* 2008, 10, 1325.

Cross-metathesis is water at room temperature

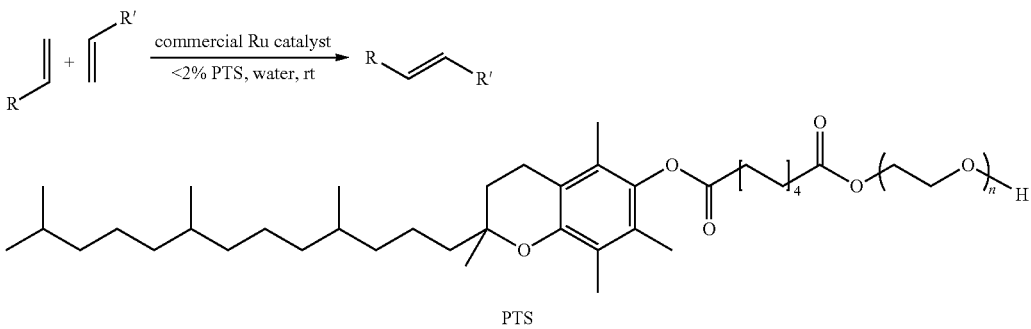

PTS

The above reactions may include asymmetric reactions using chiral substrates and reagents and/or for the preparation of chiral or achiral products.

All aspects and embodiments recited herein are only exemplary and non-limiting. It should be understood that these reactions are merely a sampling of the possible reactions that can be performed using the mixtures disclosed herein. Particular examples of these reactions follow.

EXAMPLES

Example 1

Preparation of TPGS-M-PEG-750 afford DL-α-tocopherylsuccinate (5.25 g, 99%) as a white solid. mp 68-71° C.; IR (neat): 2926, 1757, 1714, 1576, 1463, 1455, 1415, 1377, 1251, 1224, 1151, 1110, 1078, 926 cm$^{-1}$; $^1$H NMR (400 MHz, CDCl$_3$): δ 2.94 (t, J=6.8 Hz, 2H), 2.84 (t, J=6.8 Hz, 2H), 2.59 (t, J=6.8 Hz, 2H), 2.09 (s, 3H), 2.02 (s, 3H), 1.98 (s, 3H), 1.85-1.71 (m, 2H), 1.56-1.50 (m, 3H), 1.43-1.05 (m, 21H), 0.88-0.84 (m, 12H); $^{13}$C NMR (100 MHz, CDCl$_3$): δ 178.6, 171.0, 149.7, 140.7, 126.9, 125.1, 123.2, 117.6, 75.2, 39.6, 37.8, 37.7, 37.6, 37.5, 33.0, 32.9, 31.3, 29.2, 28.8, 28.2, 25.0, 24.6, 24.0, 22.9, 22.8, 21.2, 20.8, 19.95, 19.88, 13.0, 12.2, 12.0.

DL-α-Tocopherylsuccinate (2.97 g, 5.60 mmol), polyethylene glycol monomethylether-750 (4.00 g, 5.33 mmol) and p-TsOH (0.15 g, 0.79 mmol) in toluene (20 mL) were refluxed for 5 h using a Dean-Stark trap. The reaction mixture

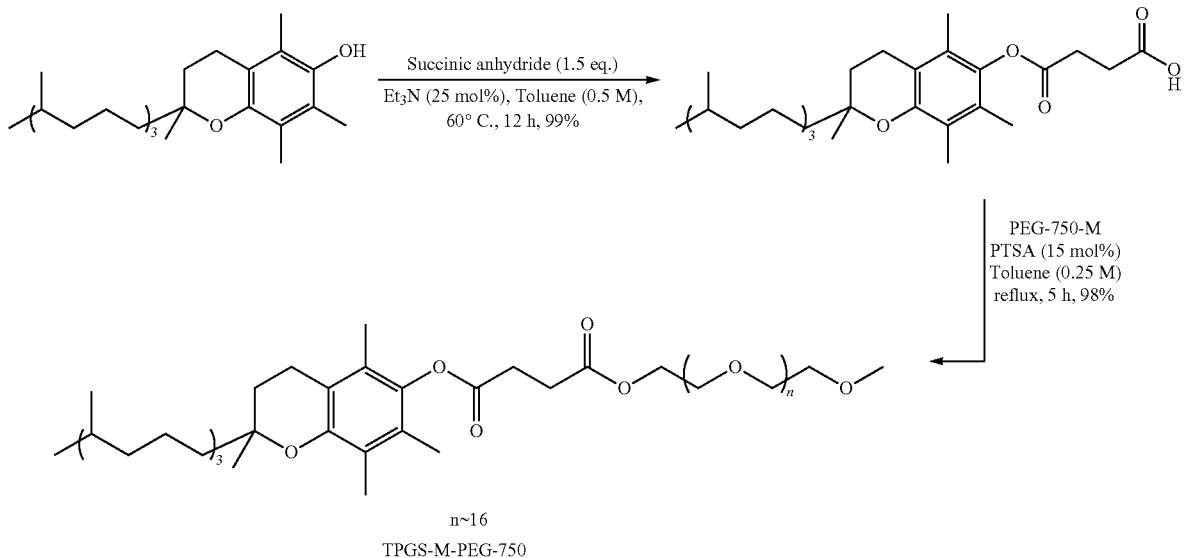

n~16
TPGS-M-PEG-750

To a solution of DL-α-Tocopherol (4.30 g, 10.00 mmol) and succinic anhydride (1.50 g, 15.00 mmol) in toluene (20 mL), Et$_3$N (0.35 mL, 2.50 mmol) was added at 22° C. with stirring, and the stirring was continued at 60° C. for 5 h. Water was added to the reaction mixture and extracted with CH$_2$Cl$_2$. The combined organic layers were washed with 1(N) HCl (3×50 mL), water (2×30 mL), dried over Na$_2$SO$_4$ and concentrated in vacuo affording a yellow liquid, which was purified by flash column chromatography on silica gel eluting with 10% EtOAc/hexane to 35% EtOAc/hexanes gradient to was poured into saturated NaHCO$_3$ solution and extracted with CH$_2$Cl$_2$. The combined organic layers were washed with saturated NaHCO$_3$ (3×50 mL), brine (2×30 mL), dried over anhydrous Na$_2$SO$_4$, and then concentrated in vacuo to afford TPGS-750-M (6.60 g, 98%) as a waxy solid. IR (neat): 2888, 1755, 1739, 1465, 1414, 1346, 1281, 1245, 1202, 1109, 947, 845 cm$^{-1}$; $^1$H NMR (400 MHz, CDCl$_3$): δ4.28-4.26 (m, 2H), 3.71-3.54 (m, PEG), 3.38 (s, 3H), 2.93 (t, J=7.2 Hz, 2H), 2.79 (t, J=7.2 Hz, 2H), 2.58 (t, J=6.8 Hz, 2H), 2.08 (s, 3H), 2.01 (s, 3H), 1.97 (s, 3H), 1.84-1.70 (m, 2H), 1.55-1.04 (m, 22H), 0.87-0.83 (m, 12H); $^{13}$C NMR (100 MHz, CDCl$_3$): δ172.2, 170.9, 149.5, 140.6, 126.7, 125.0, 123.0, 117.4, 94.5, 75.1, 72.0, 70.64, 70.56, 69.1, 64.0, 59.0, 39.4, 37.6, 37.5, 37.4, 37.3, 32.8, 32.7, 31.1, 29.2, 28.9, 28.0, 24.8, 24.5, 22.8, 22.7, 21.1, 20.6, 19.8, 19.7, 13.0, 12.1, 11.8; MS (ESI): m/z1272 (M+Na).

All examples that follow involving "TPGS-750-M" imply use of "TPGS-M-PEG-750" as surfactant. References to "TPGS-1000" imply use of TPGS-PEG-1000 (i.e., unmethylated). References to PTS imply use of unmethylated PTS-600.

Example 2

General Procedure for Ring-Closing Metathesis

Diene (0.20 mmol) and Grubbs-2 catalyst (3.4 mg, 0.004 mmol) were added into a Teflon-coated-stir-bar-containing Biotage 2-5 mL microwave reactor vial at rt, and sealed with a septum. An aliquot of TPGS-M-PEG-750/H$_2$O (2.0 mL; 2.5% TPGS-M-PEG-750 by weight; all RCM reactions were conducted at 0.1 M unless stated otherwise) was added, via syringe, and the resulting solution was allowed to stir at rt for 3 h. The homogeneous reaction mixture was then diluted with EtOAc (2 mL), filtered through a bed of silica gel, and the bed further washed (3×5 mL) with EtOAc to collect all of the cyclized material. The volatiles were removed in vacuo to afford the crude product that was subsequently purified by flash chromatography using silica gel (EtOAc/hexanes) to afford the desired products.

1-Tosyl-1,2,5,6-tetrahydropyridine

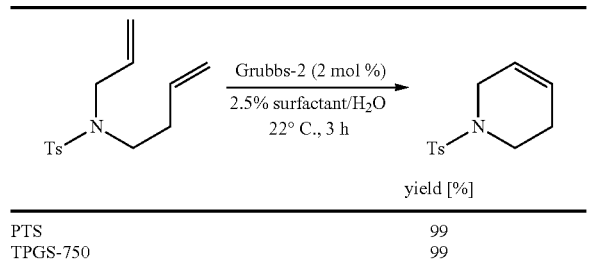

| | yield [%] |
|---|---|
| PTS | 99 |
| TPGS-750 | 99 |

The representative procedure was followed using N-allyl-N-(but-3-enyl)-4-methylbenzenesulfonamide (53 mg, 0.20 mmol) and Grubbs-2 catalyst (3.4 mg, 0.004 mmol). Column chromatography on silica gel (eluting with 5% EtOAc/hexanes) afforded the product as a white solid (47 mg, 99%). The $^1$H NMR spectral data obtained was in accord with data previously reported for this compound.

1-Tosyl-2,5,6,7-tetrahydro-1H-azepine

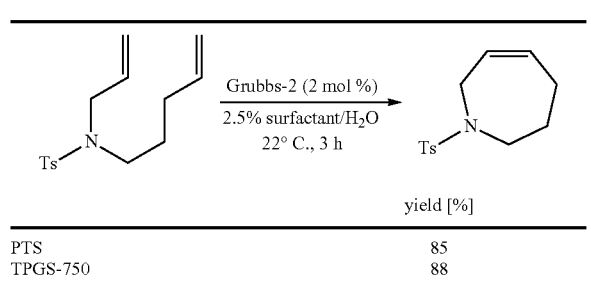

| | yield [%] |
|---|---|
| PTS | 85 |
| TPGS-750 | 88 |

The representative procedure was followed using N-allyl-4-methyl-N-(pent-4-enyl)benzenesulfonamide (56 mg, 0.20 mmol) and Grubbs-2 catalyst (3.4 mg, 0.004 mmol). Column chromatography on silica gel (eluting with 5% EtOAc/hexanes) afforded the product as a white solid (44 mg, 88%). The $^1$H NMR spectral data obtained was in accord with data previously reported for this compound.

Example 3

General Procedure for Olefin Cross-Metathesis

Alkene (0.50 mmol), acrylate (1.00 mmol)/ketone (1.50 mmol) and Grubbs-2 catalyst (8.5 mg, 0.010 mmol) were sequentially added into a Teflon-coated-stir-bar-containing Biotage 2-5 mL microwave reactor vial at rt, and sealed with a septum. An aliquot of TPGS-M-PEG-750/H$_2$O (1.0 mL; 2.5% TPGS-M-PEG-750 by weight; all cross-coupling reactions were conducted at 0.5 M unless stated otherwise) was added, via syringe, and the resulting solution was allowed to stir at rt for 12 h. The homogeneous reaction mixture was then diluted with EtOAc (2 mL), filtered through a bed of silica gel, and the bed further washed (3×5 mL) with EtOAc to collect all of the cross-coupled material. The volatiles were removed in vacuo to afford the crude product that was subsequently purified by flash chromatography on silica gel (EtOAc/hexanes) to afford the title compounds.

(E)-tert-Butyl 11-(tert-butyldimethylsilyloxy)-2-undecenoate

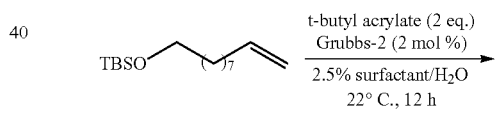

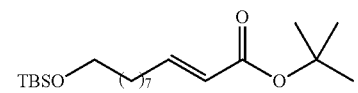

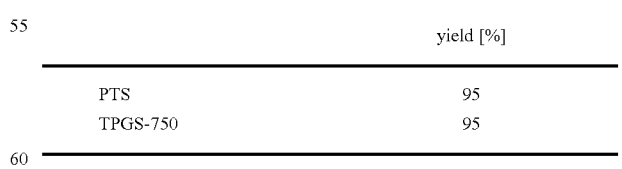

| | yield [%] |
|---|---|
| PTS | 95 |
| TPGS-750 | 95 |

The representative procedure was followed using tert-butyl (dec-9-enyloxy)dimethylsilane (135 mg, 0.50 mmol), tert-butyl acrylate (128 mg, 1.00 mmol) and Grubbs-2 catalyst (8.5 mg, 0.01 mmol). Column chromatography on silica gel (eluting with 2% EtOAc/hexanes) afforded the product as a colorless oil (176 mg, 95%).

(E)-tert-Butyl 3-(2,4-dimethylphenyl)acrylate

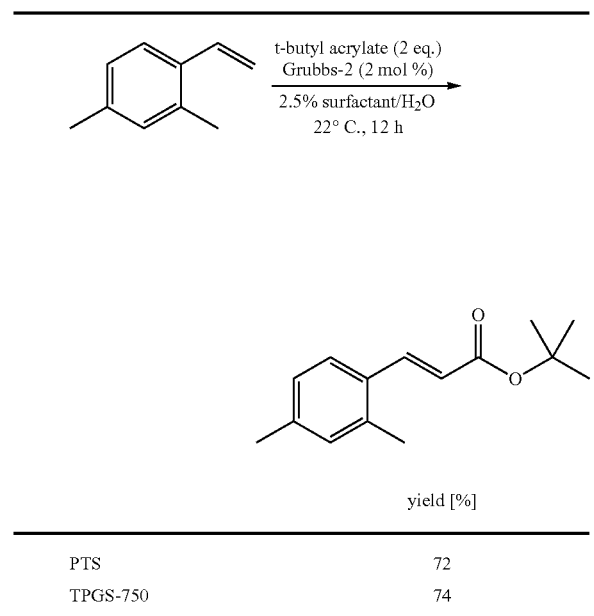

| | yield [%] |
|---|---|
| PTS | 72 |
| TPGS-750 | 74 |

The representative procedure was followed using 2,4-dimethyl-1-vinylbenzene (66 mg, 0.50 mmol), tert-butyl acrylate (128 mg, 1.00 mmol) and Grubbs-2 catalyst (8.5 mg, 0.01 mmol). Column chromatography on silica gel (eluting with 2% EtOAc/hexanes) afforded the product as a colorless oil (86 mg, 74%).

(E)-2-Adamantyl 4-(4-methoxyphenyl)-2-butenoate

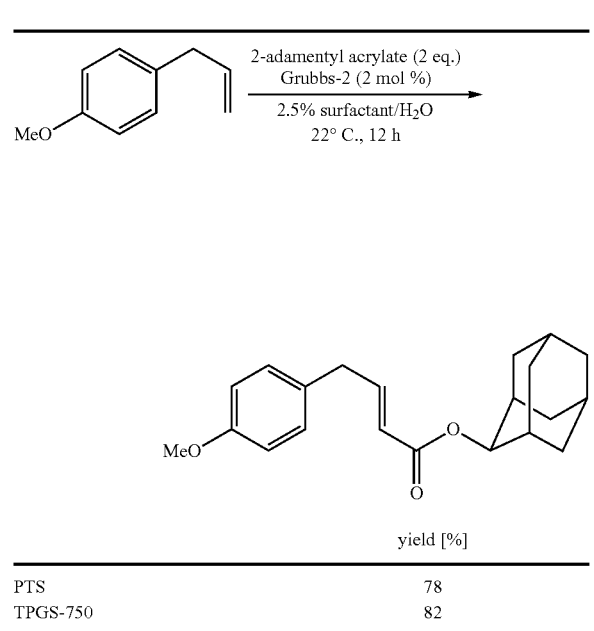

| | yield [%] |
|---|---|
| PTS | 78 |
| TPGS-750 | 82 |

The representative procedure was followed using 4-allylanisole (74 mg, 0.50 mmol), 2-adamantyl acrylate (206 mg, 1.00 mmol) and Grubbs-2 catalyst (8.5 mg, 0.01 mmol). Column chromatography on silica gel (eluting with 5% EtOAc/hexanes) afforded the product as a colorless oil (134 mg, 82%).

(E)-tert-Butyl 4-(2-(tert-butyldimethylsilyloxy)phenyl)-2-butenoate

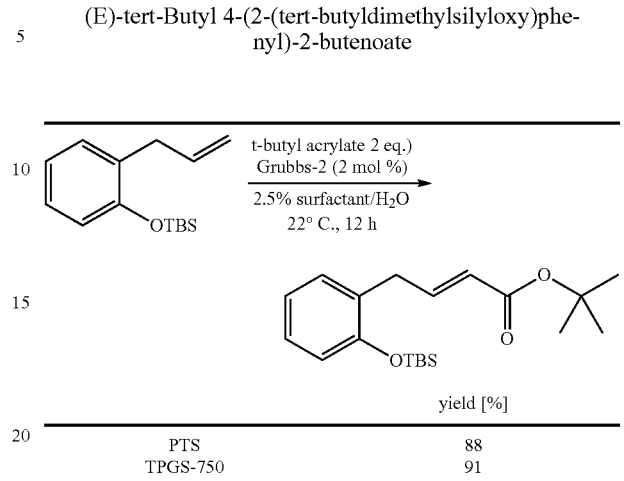

| | yield [%] |
|---|---|
| PTS | 88 |
| TPGS-750 | 91 |

The representative procedure was followed using tert-butyl (2-allylphenoxy)dimethylsilane (124 mg, 0.50 mmol), tert-butyl acrylate (128 mg, 1.00 mmol) and Grubbs-2 catalyst (8.5 mg, 0.01 mmol). Column chromatography on silica gel (eluting with 3% EtOAc/hexanes) afforded the product as a colorless oil (158 mg, 91%).

(E)-5-(2-(tert-Butyldimethylsilyloxy)phenyl)pent-3-en-2-one

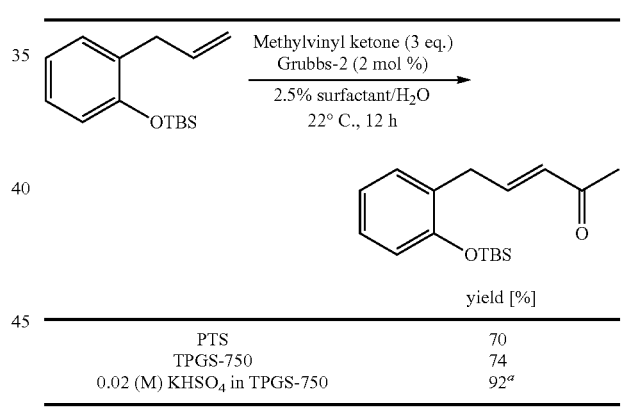

| | yield [%] |
|---|---|
| PTS | 70 |
| TPGS-750 | 74 |
| 0.02 (M) KHSO$_4$ in TPGS-750 | 92[a] |

[a] run for 4 h

The representative procedure was followed using tert-butyl (2-allylphenoxy)dimethylsilane (124 mg, 0.50 mmol), methyl vinyl ketone (106 mg, 1.50 mmol) and Grubbs-2 catalyst (8.5 mg, 0.01 mmol). Column chromatography on silica gel (eluting with 3% EtOAc/hexanes) afforded the product as a colorless oil (107 mg, 74%).

Example 4

General Procedure for Heck Coupling

The catalyst Pd[P(t-Bu)$_3$]$_2$ (5.1 mg, 0.01 mmol) and aryl iodide (0.50 mmol) were added under argon into a 5.0 mL microwave vial equipped with a large stir bar and Teflon lined septum. An aliquot of TPGS-M-PEG-750/H$_2$O (1.0 mL; 5.0% TPGS-M-PEG-750 by weight) solution, triethylamine (208 μL, 1.50 mmol), and acrylate/styrene (1.0 mmol) were added by syringe, and the resulting solution was allowed to stir at rt for 4-12 h. The homogeneous reaction mixture was then diluted with EtOAc (2 mL), filtered through a bed of silica gel, and the bed further washed (3×5 mL) with EtOAc to collect all of the coupled material. The volatiles were removed in vacuo to afford the crude product which was subsequently purified by flash chromatography on silica gel (EtOAc/hexanes) to afford the title compounds.

(E)-tert-Butyl 3-(4-methoxyphenyl)acrylate

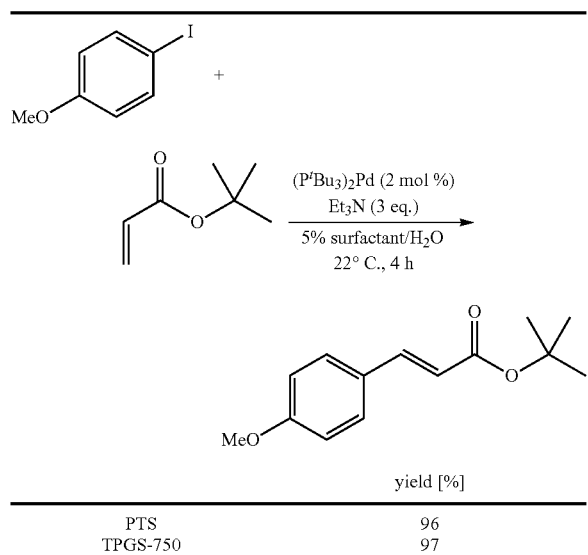

| | yield [%] |
|---|---|
| PTS | 96 |
| TPGS-750 | 97 |

Following the general procedure using 4-methoxyiodobenzene (117 mg, 0.50 mmol) and tert-butyl acrylate (145 µL, 1.00 mmol), the reaction was stirred for 4 h at rt. Column chromatography on silica gel (eluting with 3% EtOAc/hexanes) afforded the product as a colorless oil (113 mg, 97%).

(E)-1-(2,4-Dimethylstyryl)-2-methoxynaphthalene

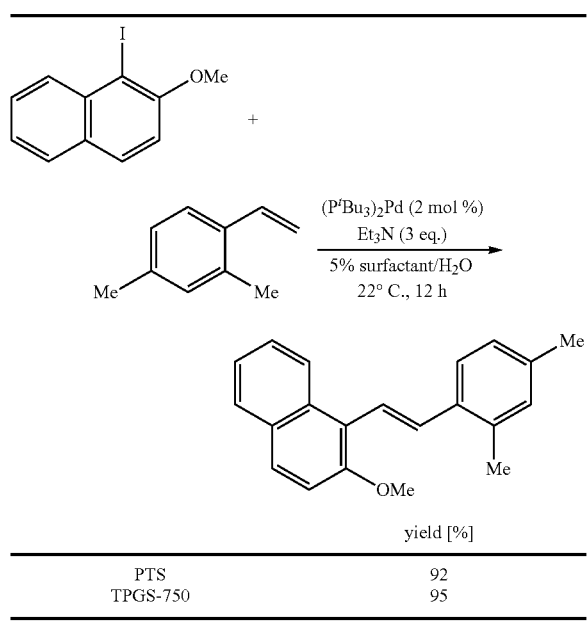

| | yield [%] |
|---|---|
| PTS | 92 |
| TPGS-750 | 95 |

Following the general procedure using 1-iodo-2-methoxynaphthalene (142 mg, 0.50 mmol) and 2,4-dimethylstyrene (132 µL, 1.0 mmol), the reaction was stirred for 12 h at rt. Column chromatography on silica gel (eluting with 5% EtOAc/hexanes) afforded the product as a tan semi-solid (137 mg, 95%).

Example 5

General Procedure for Sonogashira Coupling

The catalyst Pd(CH$_3$CN)$_2$Cl$_2$ (1.3 mg, 0.005 mmol) and XPhos (6.2 mg, 0.013 mmol) were added under argon into a 5.0 mL microwave vial equipped with a large stir bar and Teflon lined septum. An aliquot of TPGS-M-PEG-750/H$_2$O (1.0 mL; 3.0% TPGS-M-PEG-750 by weight) solution, triethylamine (140 µL, 1.00 mmol), aryl bromide (0.50 mmol) and alkyne (0.75 mmol) were added by syringe, and the resulting solution was allowed to stir at rt for 21-25 h. The homogeneous reaction mixture was then diluted with EtOAc (2 mL), filtered through a bed of silica gel, and the bed further washed (3×5 mL) with EtOAc to collect all of the coupled material. The volatiles were removed in vacuo to afford the crude product which was subsequently purified by flash chromatography on silica gel (EtOAc/hexanes) to afford the title compounds.

2-(Cyclohexenylethynyl)naphthalene

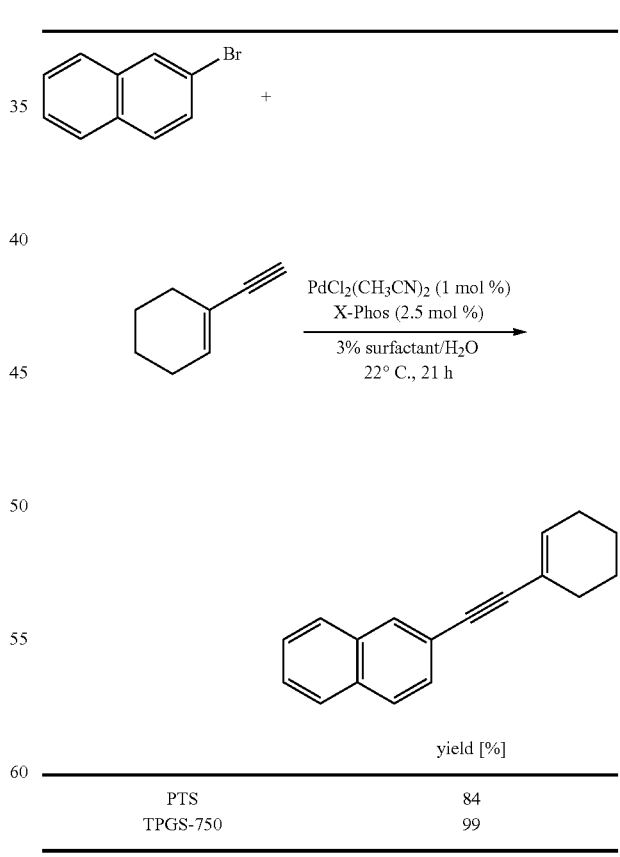

| | yield [%] |
|---|---|
| PTS | 84 |
| TPGS-750 | 99 |

Following the general procedure using 2-bromonaphthalene (103 mg, 0.50 mmol) and 1-ethynylcyclohex-1-ene (100 µL, 0.85 mmol), the reaction was stirred for 21 h at rt. Column chromatography on silica gel (eluting with 1% EtOAc/hexanes) afforded the product as an off-white solid (115 mg, 99%).

1-(6-Chlorohex-1-ynyl)-4-methoxybenzene

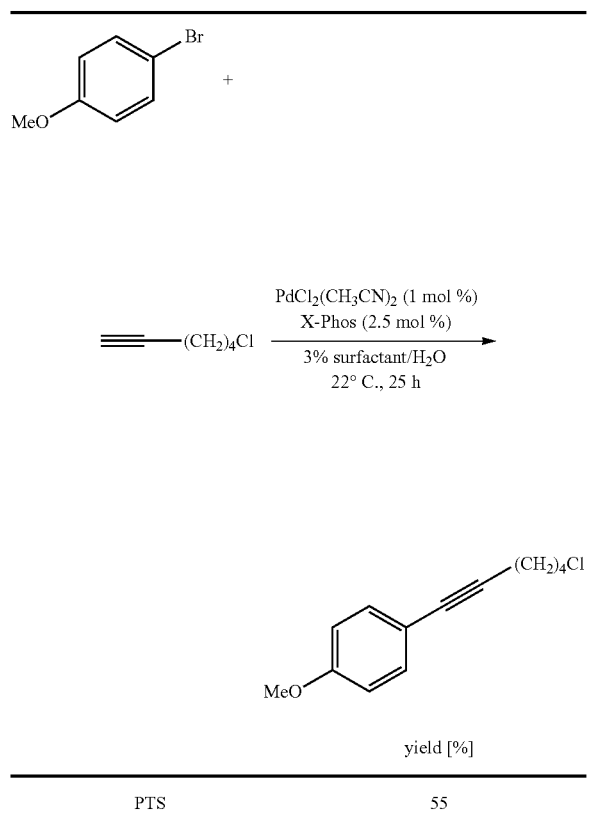

| | yield [%] |
|---|---|
| PTS | 55 |
| TPGS-750 | 66 |

Following the general procedure using 4-bromoanisole (60 mg, 0.48 mmol) and 6-chloro-1-hexyne (90 μL, 0.74 mmol), the reaction was stirred for 25 h at rt. Column chromatography on silica gel (eluting with 1% EtOAc/hexanes) afforded the product as a pale yellow oil (70 mg, 66%).

Example 6

General Procedure for Aminations of Aromatics (Buchwald-Hartwig Amination)

The catalyst [(π-allyl)PdCl]₂ (2.1 mg, 0.006 mmol), cBRIDP (2) (7.6 mg, 0.022 mmol), KO-t-Bu (184 mg, 1.56 mmol) and amine (1.20 mmol) were added under argon into a 5.0 mL microwave vial equipped with a large stir bar and Teflon lined septum. An aliquot of TPGS-M-PEG-750/H₂O (1.0 mL; 2.0% TPGS-M-PEG-750 by weight) solution and aryl bromide (1.00 mmol) were added by syringe, and the resulting solution was allowed to stir at rt for 19-20 h. The homogeneous reaction mixture was then diluted with EtOAc (2 mL), filtered through a bed of silica gel, and the bed further washed (3×5 mL) with EtOAc to collect all of the coupled material. The volatiles were removed in vacuo to afford the crude product which was subsequently purified by flash chromatography on silica gel (EtOAc/hexanes) to afford the title compounds.

N-(m-Tolyl)-3-aminopyridine

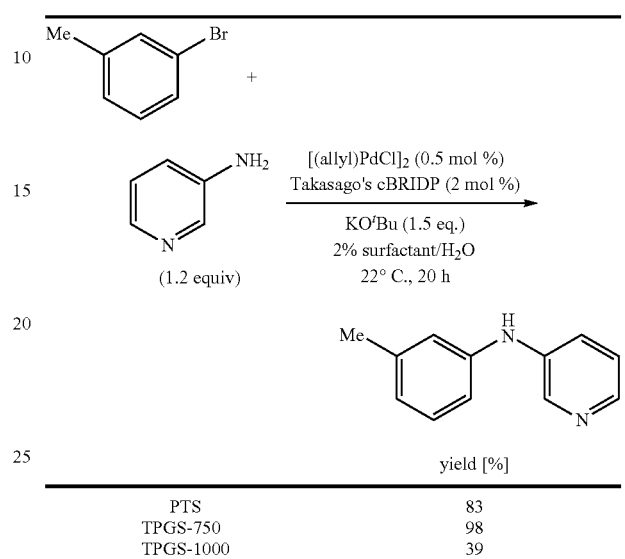

| | yield [%] |
|---|---|
| PTS | 83 |
| TPGS-750 | 98 |
| TPGS-1000 | 39 |

Following the general procedure using 3-bromotoluene (121 μL, 1.00 mmol) and 3-aminopyridine (113 mg, 1.20 mmol), the reaction was stirred for 20 h at rt. Column chromatography on silica gel (eluting with 40% EtOAc/hexanes) afforded the product as an off-white solid (180 mg, 98%).

2,6-Dimethyl-N-(m-tolyl)aniline

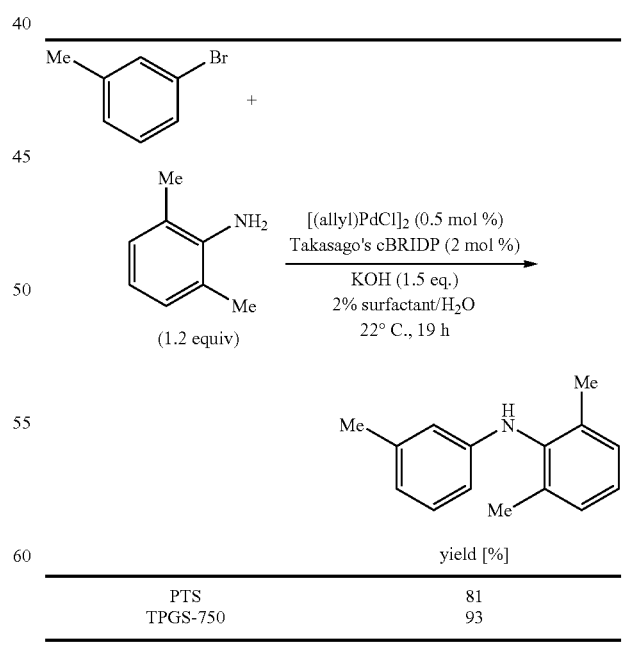

| | yield [%] |
|---|---|
| PTS | 81 |
| TPGS-750 | 93 |

Following the general procedure using 3-bromotoluene (121 μL, 1.00 mmol) and 2,6-dimethylaniline (148 μL, 1.20 mmol), the reaction was stirred for 19 h at rt. Column chromatography on silica gel (eluting with 30% EtOAc/hexanes) afforded the product as an off-white solid (196 mg, 93%).

Example 7

General Procedure for Suzuki-Miyaura Couplings with Allylic Ethers

Allylic phenyl ether (0.25 mmol), Arylboronic acid (0.38 mmol), and PdCl$_2$(DPEphos) (0.005 mmol, 3.6 mg) (or PdCl$_2$ (Dt-BPF)) were sequentially added under air to a reaction tube equipped with a stir bar and a septum. Degassed TPGS-M-PEG-750 solution (0.8 mL, 2 wt %), and Et$_3$N (0.75 mmol, 0.1 mL) were added by syringe and vigorously stirred for 5-20 h. After the reaction, the contents of the flask were diluted with brine and extracted with EtOAc. The solution obtained was dried over anhydrous MgSO$_4$, filtered, and concentrated by rotary evaporation. The residue was purified by flash chromatography eluting with hexane/EtOAc to afford the product.

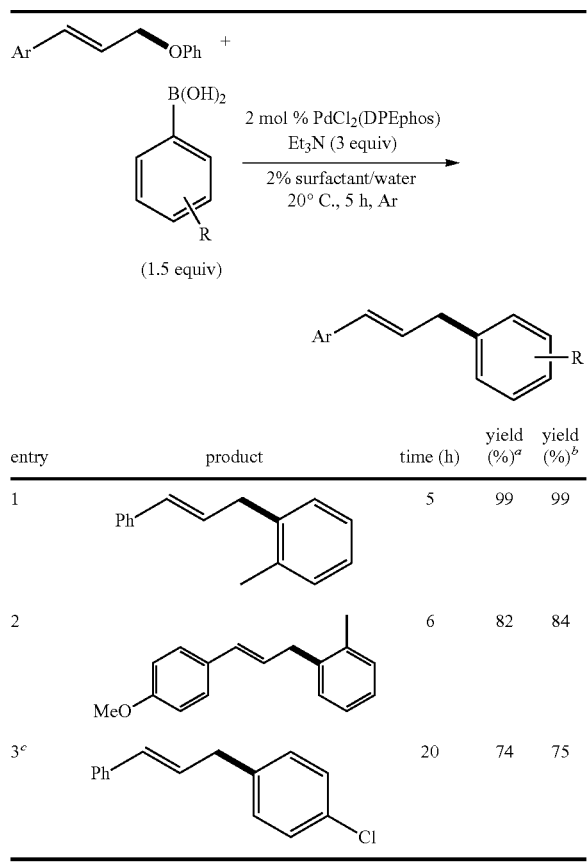

[a]Using PTS.
[b]Using TPGS-750.
[c]6 mol % D$^t$BPF.

1-Cinnamyl-2-methylbenzene

Following the general procedure using cinnamyloxybenzene (53 mg, 0.25 mmol), o-tolylboronic acid (51 mg, 0.38 mmol), and PdCl$_2$(DPEphos) (0.005 mmol, 3.6 mg), the reaction was stirred for 5 h at rt. Column chromatography on silica gel (eluting with 3% EtOAc/hexanes) afforded the product as a colorless liquid (51 mg, 99%).

(E)-1-(3-(4-Methoxyphenyl)allyl)-2-methylbenzene

Following the general procedure using (E)-1-methoxy-4-(3-phenoxyprop-1-enyl)benzene (60 mg, 0.25 mmol), o-tolylboronic acid (51 mg, 0.38 mmol) and PdCl$_2$(DPEphos) (0.015 mmol, 11 mg), the reaction was stirred for 6 h at rt. Column chromatography on silica gel (eluting with 3% EtOAc/hexanes) afforded the product as a colorless liquid (51 mg, 84%).

1-Chloro-4-cinnamylbenzene

Following the general procedure using cinnamyloxybenzene (53 mg, 0.25 mmol), 4-chlorophenylboronic acid (58 mg, 0.38 mmol) and PdCl$_2$(D-t-BPF) (0.015 mmol, 9.8 mg), the reaction was stirred for 20 h at rt. Column chromatography on silica gel (eluting with 3% EtOAc/hexanes) afforded the product as a colorless liquid (43 mg, 75%).

Example 8

Aminations of Allylic Alcohols

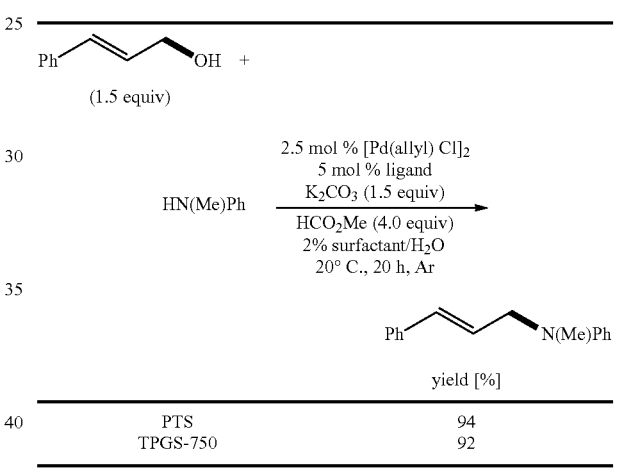

| | yield [%] |
|---|---|
| PTS | 94 |
| TPGS-750 | 92 |

N-Cinnamyl-N-methylaniline

Cinnamyl alcohol (100 mg, 0.75 mmol), N-methylaniline (53 mg, 0.50 mmol), dppf (14 mg, 0.025 mmol), K$_2$CO$_3$ (207 mg, 1.5 mmol) and [Pd(allyl)Cl]$_2$ (4.5 mg, 0.0125 mmol) were sequentially added under argon to a reaction tube equipped with a stir bar and a septum. Degassed TPGS-M-PEG-750 solution (1.0 mL, 2 wt %), and HCO$_2$Me (0.12 mL, 2.0 mmol) were added by syringe and vigorously stirred for 20 h. After the reaction, the contents of the flask were diluted with brine and extracted with EtOAc. The solution obtained was dried over anhydrous MgSO$_4$, filtered, and concentrated by rotary evaporation. The residue was purified by flash chromatography eluting with 10% EtOAc/hexanes to afford the product as a pale yellow liquid (102 mg, 92%).

Example 9

General Procedure for Aminations of Allylic Ethers

Allylic phenyl ether (0.5 mmol), amine (0.75 mmol), DPEphos (0.005 mmol, 2.7 mg), K$_2$CO$_3$ (0.75 mmol, 103 mg) and [Pd(allyl)Cl]$_2$ (0.0025 mmol, 0.9 mg) were sequentially added under air to a reaction tube equipped with a stir bar and a septum. Degassed TPGS-M-PEG-750 solution (1.0 mL, 2 wt %), and HCO$_2$Me (2.0 mmol, 0.12 mL) were added by syringe and vigorously stirred for 0.5-2.5 h. After the reaction, the contents of the flask were diluted with brine and extracted with EtOAc. The solution obtained was dried over anhydrous MgSO$_4$, filtered, and concentrated by rotary evaporation. The residue was purified by flash chromatography eluting with hexane/EtOAc to afford the product.

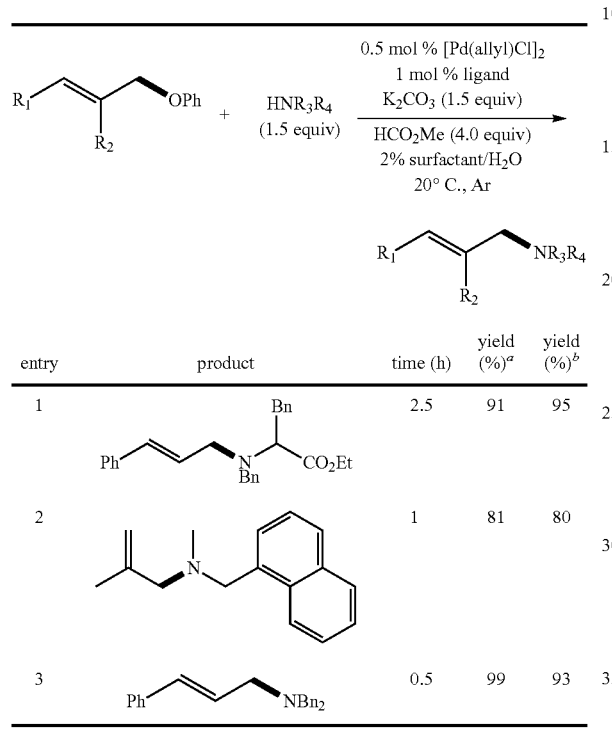

N-Methyl-N-(2-methallyl)-1-naphthylmethylamine

Following the general procedure using (2-methylallyloxy)benzene (74 mg, 0.50 mmol) and N-methyl-N-naphthylmethylamine (128 mg, 0.75 mmol), the reaction was stirred for 1 h at rt. Column chromatography on silica gel (eluting with 10% EtOAc/hexanes) afforded the product as a colorless liquid (88 mg, 80%).

(E)-N-Benzyl-N-(3-phenyl-2-propenyl)-3-phenylalanine ethyl ester

Following the general procedure using cinnamyloxybenzene (105 mg, 0.50 mmol) and ethyl 2-(benzylamino)-3-phenylpropanoate (212 mg, 0.75 mmol), the reaction was stirred for 2.5 h at rt. Column chromatography on silica gel (eluting with 10% EtOAc/hexanes) afforded the product as a pale yellow liquid (190 mg, 95%).

(E)-N,N-Dibenzyl-3-phenylprop-2-en-1-amine

Following the general procedure using cinnamyloxybenzene (105 mg, 0.50 mmol) and dibenzylamine (148 mg, 0.75 mmol), the reaction was stirred for 0.5 h at rt. Column chromatography on silica gel (eluting with 8% EtOAc/hexanes) afforded the product as a pale yellow liquid (145 mg, 93%).

Example 10

C—H Activation (Fujiwara-Moritani reactions)

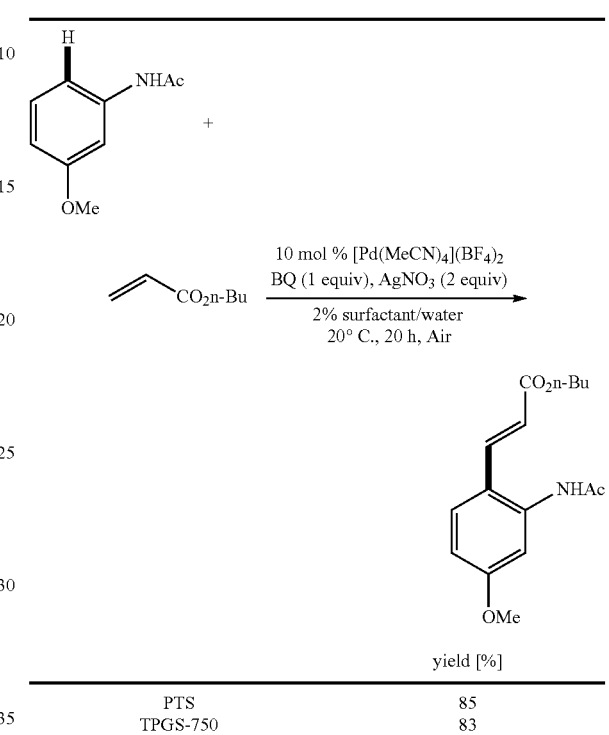

| | yield [%] |
|---|---|
| PTS | 85 |
| TPGS-750 | 83 |

(E)-Butyl 3-(2-acetamido-4-methoxyphenyl)acrylate

N-(3-methoxy phenyl)acetamide (41 mg, 0.25 mmol), n-butyl acrylate (64 mg, 0.50 mmol), 1,4-benzoquinone (27 mg, 0.25 mmol), AgNO$_3$ (85 mg, 0.5 mmol), and [Pd(MeCN)$_4$](BF$_4$)$_2$ (11 mg, 0.025 mmol) were sequentially added under air to a reaction tube equipped with a stir bar and a septum. A degassed aqueous solution containing TPGS-M-PEG-750 (1.0 mL, 2 wt %) was added by syringe and the resulting mixture vigorously stirred for 20 h. After this time, the contents of the flask were quenched with aqueous NaHCO$_3$ and extracted with EtOAc. The solution obtained was filtered through the plug of silica gel and anhydrous MgSO$_4$, and then concentrated by rotary evaporation. The residue was purified by flash chromatography, eluting with 50% EtOAc/hexanes to afford the product as an off-white solid (60 mg, 83%).

Example 11

General Procedure for Silylation

A 1 dram vial containing a strong magnetic stir bar was loaded with PdCl$_2$(DPEphos) (6 mol %: 10.8 mg, 15 µmol), allylic phenyl ether (0.25 mmol) and brought into a glovebag. After an atmosphere of argon was applied, hexamethyldisilane (77 µL, 0.38 mmol)/1,2-diphenyltetramethyldisilane (2b, 101.4 mg, 0.38 mmol), NEt$_3$ (139 µL, 1.0 mmol) and 2% TPGS-M-PEG-750/H$_2$O (1.5 mL) were added via syringe. The vial was immediately closed with a Teflon coated cap and vigorously stirred for 20 h at rt. The reaction mixture was poured into brine (2 mL) and extracted with EtOAc (3×2 mL). All organic phases were collected, dried over anhydrous Na₂SO₄, filtered through a short plug of silica gel and the solvent removed by a constant stream of argon. The residue was loaded on silica gel and purified by flash chromatography eluting with hexanes/EtOAc to afford the product.

| entry | product | E:Z (l:b) | yield (%)[a] | yield (%)[b] |
|---|---|---|---|---|
| 1 | Ph-CH=CH-CH₂-SiMe₂Ph | 25:1 (10:1) | 91 | 91 |
| 2 | (2-MeO-C₆H₄)-CH=CH-CH₂-SiMe₂Ph | 25:1 (25:1) | 87 | 89 |
| 3 | (3-MeO-C₆H₄)-CH=CH-CH₂-TMS | 25:1 (9:1) | 90 | 88 |

[a]Using PTS.
[b]Using TPGS-750.

Cinnamyldimethyl(phenyl)silane

Following the general procedure, using (E)-cinnamyl phenyl ether (52.6 mg, 0.25 mmol), 1,2-diphenyltetramethyldisilane (101.4 mg, 0.38 mmol), PdCl₂(DPEphos) (10.8 mg, 15 µmol), 2% TPGS-M-PEG-750/H₂O (1.5 mL) and NEt₃ (139 µL, 1.0 mmol), silica gel chromatography (hexanes) yielded the product as a colorless oil (57.4 mg, 91%).

(E)-(3-(2-Methoxyphenyl)allyl)dimethyl(phenyl) silane

Following the general procedure, using (E)-1-methoxy-2-(3-phenoxyprop-1-enyl)benzene (60.1 mg, 0.25 mmol), 1,2-diphenyltetramethyldisilane (101.4 mg, 0.38 mmol), PdCl₂(DPEphos) (10.8 mg, 15 µmol), 2% TPGS-M-PEG-750/H₂O (1.5 mL) and NEt₃ (139 µL, 1.0 mmol), silica gel chromatography (0-10% EtOAc/hexanes) yielded the product as a colorless oil (62.8 mg, 89%).

(E)-(3-(3-Methoxyphenyl)allyl)trimethylsilane

Following the general procedure, using (E)-1-methoxy-3-(3-phenoxyprop-1-enyl)benzene (60.1 mg, 0.25 mmol), hexamethyldisilane (77 µL, 0.38 mmol), PdCl₂(DPEphos) (10.8 mg, 15 µmol), 2% TPGS-M-PEG-750/H₂O (1.5 mL) and NEt₃ (139 µL, 1.0 mmol), silica gel chromatography (0-10% EtOAc/hexanes) yielded the product as a colorless liquid (48.5 mg, 88%).

Example 12

C—H Activation/Arylation

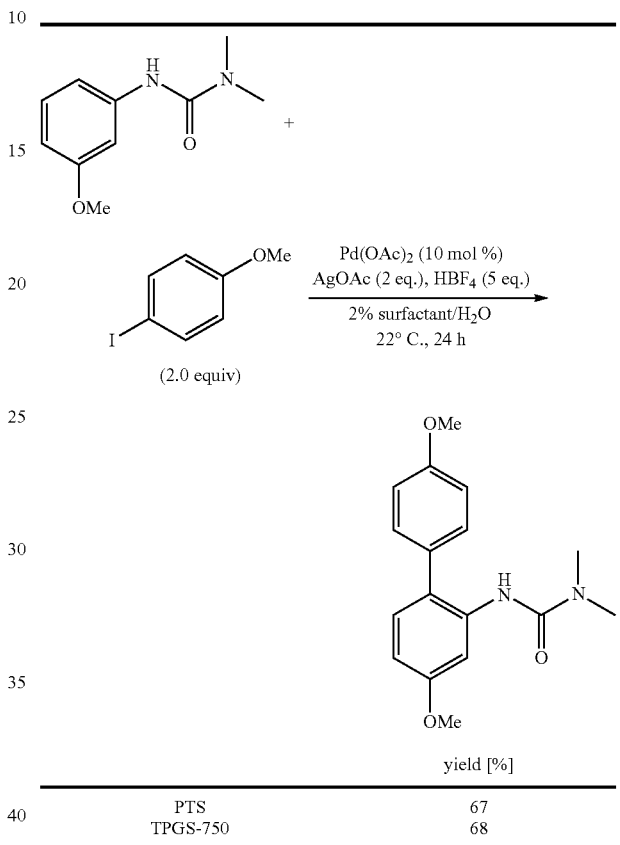

| | yield [%] |
|---|---|
| PTS | 67 |
| TPGS-750 | 68 |

3-(4,4'-Dimethoxybiphenyl-2-yl)-1,1-dimethylurea (Using TPGS-M-PEG-750)

3-(3-Methoxyphenyl)-1,1-dimethylurea (49 mg, 0.25 mmol), 1-iodo-4-methoxybenzene (117 mg, 0.50 mmol), AgOAc (0.5 mmol, 83 mg), and Pd(OAc)₂ (0.025 mmol, 5.6 mg), were sequentially added under air to a reaction tube equipped with a stir bar and septum. An aliquot of TPGS-M-PEG-750/H₂O (1.0 mL; 2.0% TPGS-M-PEG-750 by weight) solution, and 48 wt % aqueous HBF₄ solution (1.25 mmol, 0.16 mL) were added by syringe and stirred vigorously for 24 h. After the reaction, the contents of the flask were quenched with NaHCO₃ and extracted with EtOAc. The solution obtained was dried over anhydrous MgSO₄ and concentrated by rotary evaporation. The residue was purified by flash chromatography eluting with 1:1 EtOAc/hexanes to afford the product (51 mg, 68%) as a white solid.

General Procedure for C—H Activation/Arylation of Aryl Ureas

The aryl urea (0.25 mmol), aryl iodide (0.5 mmol), AgOAc (0.5 mmol, 83 mg), and Pd(OAc)₂ (0.025 mmol, 5.6 mg) were sequentially added under air to a reaction tube equipped with a stir bar and a septum. An aqueous solution containing the surfactant (Brij 35; 1.0 mL, 2 wt %), and 48 wt % HBF₄ (1.25 mmol, 0.16 mL) was added by syringe and the resulting mixture vigorously stirred for 20 h at ambient temperature. After this time, the contents of the flask were quenched with aqueous NaHCO₃ and extracted with EtOAc. The solution obtained was filtered through the plug of silica gel and anhydrous MgSO₄, and then concentrated by rotary evaporation. The residue was purified by flash chromatography, eluting with hexane/EtOAc to afford the product.

Example 13

Suzuki-Miyaura Couplings

3-Phenylbenzonitrile

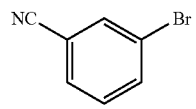

+

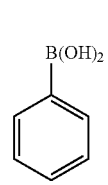

2 mol % Pd(dtbpf)Cl₂
Et₃N (3 equiv)
───────────────→
2% surfactant/water
20° C., 2 h, Ar

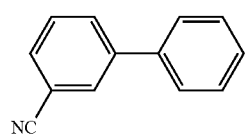

| | yield [%] |
|---|---|
| PTS | 78 |
| TPGS-750 | 93 |

3-Bromobenzonitrile (91 mg, 0.5 mmol), phenylboronic acid (91 mg, 0.75 mmol), and Pd(dtbpf)Cl₂ (6 mg, 0.01 mmol) were added to a reaction tube equipped with a magnetic stir bar. Under a positive flow of argon while stirring, surfactant solution (1.0 mL, 2 wt % TPGS-M-PEG-750 in water), and Et₃N (0.21 mL, 1.5 mmol) were added by syringe and stirred vigorously for 2 h. The reaction mixture was then diluted with brine and extracted with EtOAc. The solution obtained was dried over anhydrous MgSO₄ and concentrated by rotary evaporation. The residue was purified by flash column chromatography eluting with 20% CH₂Cl₂/hexanes to afford the product (83 mg, 93%) as a slightly yellow oil.

4-Methoxy-2',4',6'-tri-iso-propylbiphenyl

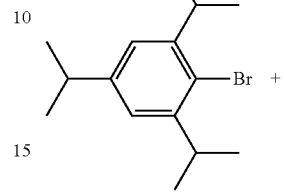

+

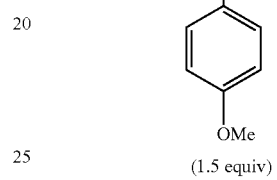
(1.5 equiv)

2 mol % Pd(dtbpf)Cl₂
Et₃N (3 equiv)
───────────────→
2% surfactant/water
20° C., 24 h, Ar

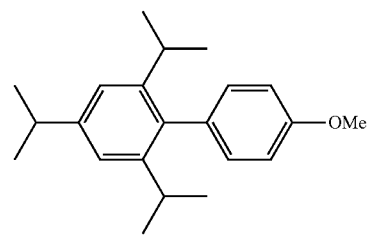 [SMILES: COc1ccc(-c2c(C(C)C)cc(C(C)C)cc2C(C)C)cc1]

| | yield [%] |
|---|---|
| PTS | 76 |
| TPGS-750 | 88 |
| TPGS-1000 | 77 |

4-Methoxyphenylboronic acid (152 mg, 1.00 mmol), and Pd(dtbpf)Cl₂ (6 mg, 0.01 mmol) were added to a reaction tube equipped with a magnetic stir bar. Under a positive flow of argon while stirring, surfactant solution (1.0 mL, 2 wt % TPGS-M-PEG-750 in water), 2,4,6-triisopropylbenzene (126 µL, 0.50 mmol), and Et₃N (0.21 mL, 1.5 mmol) were added by syringe and stirred vigorously for 24 h. The reaction mixture was then diluted with brine and extracted with EtOAc. The solution obtained was dried over MgSO₄ and concentrated by rotary evaporation. The residue was purified by flash column chromatography eluting with 5% CH₂Cl₂/hexanes to afford the product (137 mg, 88%) as a white solid.

Example 14

Click Chemistry

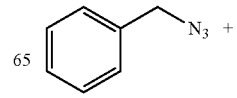 +

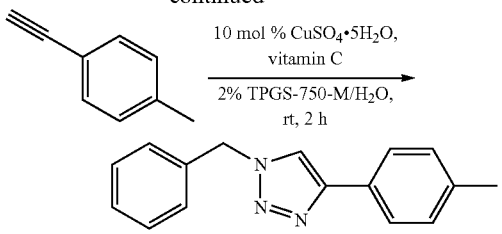

To a 5 mL vial is added 2 mL of 2 weight % of the surfactant. Benzyl azide (0.5 mmol, 66.7 mg) is added to the solution. 4-Tolylacetylene (0.5 mmol, 58.1 mg) is added to the mixture. The copper catalyst is prepared by adding CuSO$_4$·5H$_2$O (10 mol % 0.05 mmol, 12.5 mg) and ascorbic acid (12 mol %, 0.06 mmol, 10.6 mg) to 1 mL of DI water. Alternatively, catalyst can be made in bulk at the concentration described. 1 mL of the catalyst solution is added to the reaction mixture, and the solution is stirred for 1.5 h at ambient temperature. The reaction is allowed to proceed until complete. After stirring, the vial is removed and placed in an ice bath for 30 minutes. The product is isolated by filtration; washed with brine. The product is filtered and allowed to dry to obtain about 85-95% yield. See for example, Kolb, H. C.; Finn, M. G.; Sharpless, K. B. Angew. Chem., Int. Ed. Engl. 2001, 40, 2004-2021.

Example 15

Borylation Reactions

General procedure for borylations of aryl bromides in 2% TPGS-750-M/water: A 10 mL glass vial containing a strong stir bar was charged with Pd(P$^t$Bu$_3$)$_2$ (7.7 mg, 0.015 mmol), B$_2$pin$_2$ (140 mg, 0.55 mmol) and KOAc (147 mg, 1.5 mmol). The vial was capped with a rubber septum and placed under an Argon atmosphere, followed by the addition of 1.0 mL of 2% TPGS-750-M/water. After 10 min of vigorous stirring, the aryl bromide (0.5 mmol) was added, followed by an additional 1.0 mL of solvent. Conversion was monitored by GC/FID and/or TLC. After the indicated time, the reaction was extracted with EtOAc (3×2 mL). The combined organic layers were filtered through a short plug of SiO$_2$ and the solvent was removed under reduced pressure. The residue was purified by flash chromatography eluting with EtOAc/hexanes to afford the product.

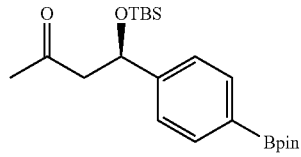

(R)-4-((tert-Butyldimethylsilyl)oxy)-4-(4-(4,4,5,5-tetramethyl-1,3,2-dioxaborolan-2-yl)phenyl)-butan-2-one Following the general procedure, using (R)-4-(4-bromophenyl)-4-((tert-butyldimethylsilyl)oxy)butan-2-one (179 mg, 0.5 mmol), Pd(P$^t$Bu$_3$)$_2$ (7.7 mg, 0.015 mmol), B$_2$pin$_2$ (140 mg, 0.55 mmol), and KOAc (147 mg, 1.5 mmol) in 2 mL of 2% TPGS-750-M/H$_2$O, GC/FID and TLC monitoring indicated complete conversion after an overall reaction time of 9 h. Workup according to the general procedure and flash column chromatography on silica (12 g, 2-10% EtOAc/hexanes) afforded the title compound as a colorless oil (165 mg, 82% yield). R$_f$=0.25 (10% EtOAc/hexanes); $^1$H NMR (500 MHz, CDCl$_3$) δ 7.73 (d, J=8.0 Hz, 2H), 7.31 (d, J=8.0 Hz, 2H), 5.13 (dd, J=9.0, 4.0 Hz, 1H), 2.89 (dd, J=14.5, 9.0 Hz, 1H), 2.48 (dd, J=14.5, 4.0 Hz, 1H), 2.11 (s, 3H), 1.31 (s, 12H), 0.81 (s, 9H), −0.03 (s, 3H), −0.22 (s, 3H); $^{13}$C NMR (125 MHz, CDCl$_3$) δ 207.2, 147.8, 135.0, 125.3, 83.9, 72.1, 54.4, 32.0, 25.9, 25.1, 25.0, 18.2, −4.5, −5.1; HR-MS(ESI): calcd. For C$_{22}$H$_{37}$BO$_4$NaSi (M+Na$^+$): 427.2452; found: 427.2444.

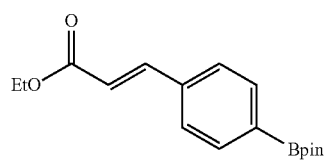

(E)-Ethyl 3-(4-(4,4,5,5-tetramethyl-1,3,2-dioxaborolan-2-yl)phenyl)acrylate

Following the general procedure, using (E)-ethyl 3-(4-bromophenyl)acrylate (128 mg, 0.5 mmol), Pd(P$^t$Bu$_3$)$_2$ (7.7 mg, 0.015 mmol), B$_2$pin$_2$ (140 mg, 0.55 mmol), and KOAc (147 mg, 1.5 mmol) in 2 mL of 2% TPGS-750-M/H$_2$O, GC/FID and TLC monitoring indicated complete conversion after an overall reaction time of 6 h. Workup according to the general procedure and flash column chromatography on silica (12 g, 2-10% EtOAc/hexanes) afforded the title compound as a colorless oil (116 mg, 77% yield). R$_f$=0.21 (10% EtOAc/hexanes); $^1$H NMR (500 MHz, CDCl$_3$) δ 7.83 (d, J=8.0 Hz, 2H), 7.70 (d, J=16.1 Hz, 1H), 7.53 (d, J=8.2 Hz, 2H), 6.50 (d, J=16.0 Hz, 1H), 4.27 (q, J=7.1 Hz, 2H), 1.36 (s, 12H), 1.34 (t, J=7.0 Hz, 3H); $^{13}$C NMR (125 MHz, CDCl$_3$) δ 167.0, 144.6, 137.1, 135.4, 127.4, 119.3, 84.2, 60.7, 25.0, 14.5; HR-MS (ESI): calcd. For C$_{17}$H$_{23}$$^{10}$BO$_4$ (M$^+$): 301.1731; found: 301.1740.

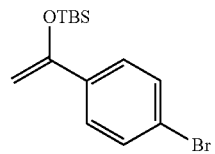 [SMILES: C=C(O[Si](C)(C)C(C)(C)C)c1ccc(Br)cc1]

((1-(4-Bromophenyl)vinyl)oxy)(tert-butyl)-dimethylsilane

A 250 mL round bottom flask was charged with 4-bromoacetophenone (1.99 g, 10.0 mmol), TBSCl (6.03 g, 40.0 mmol) and NaI (6.00, 40 mmol). The flask was capped with a rubber septum and placed under an atmosphere of Argon. After the addition of 200 mL MeCN, NEt$_3$ (6.13 mL, 44.0 mmol) was introduced and the reaction mixture was stirred for 16 h at rt until TLC monitoring indicated complete conversion. The reaction mixture was poured onto sat. NaHCO$_3$ solution and extracted with EtOAc (3×40 mL). The combined organic extracts were washed with brine, dried over anhydrous Na$_2$SO$_4$, and evaporated to yield a brown slurry. Hexanes was added and the obtained heterogeneous mixture was filtered through a short plug of silica using hexanes to afford the title compound as a colorless oil (3.02 g, 96% yield). $R_f$=0.49 (1% EtOc/hexanes); $^1$H NMR (500 MHz, CDCl$_3$) δ 7.47 (d, J=8.5 Hz, 2H), 7.44 (d, J=8.5 Hz, 2H), 4.88 (s, 1H), 4.44 (s, 1H), 1.00 (s, 9H), 0.21 (s, 6H); $^{13}$C NMR (125 MHz, CDCl$_3$) δ 155.2, 137.0, 131.4, 127.1, 122.4, 91.6, 26.0, 18.5, −4.4; HR-MS(ESI): calcd. For C$_{14}$H$_{21}$OBrSi (M$^+$): 312.0545; found: 312.0542.

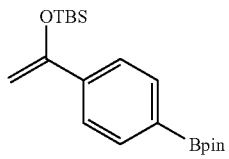

tert-Butyldimethyl((1-(4-(4,4,5,5-tetramethyl-1,3,2-dioxaborolan-2-yl)-phenyl)-vinyl)oxy)-silane Following the general procedure, using (1-(4-bromophenyl)vinyl)oxy)(tert-butyl)-dimethylsilane (157 mg, 0.5 mmol), Pd(P$^t$Bu$_3$)$_2$ (7.7 mg, 0.015 mmol), B$_2$pin$_2$ (140 mg, 0.55 mmol), and KOAc (147 mg, 1.5 mmol) in 2 mL of 2% TPGS-750-M/H$_2$O, GC/FID and TLC monitoring indicated complete conversion after an overall reaction time of 2.5 h. Workup according to the general procedure and flash column chromatography on silica (12 g, 3% EtOAc/hexanes) afforded the title compound as a colorless (153 mg, 77% yield). $R_f$=0.51 (10% EtOc/hexanes); $^1$H NMR (500 MHz, CDCl$_3$) δ 7.77 (d, J=8.0 Hz, 2H), 7.60 (d, J=8.0 Hz, 2H), 4.95 (s, 1H), 4.47 (s, 1H), 1.35 (s, 12H), 1.00 (s, 9H), 0.20 (s, 6H); $^{13}$C NMR (125 MHz, CDCl$_3$) δ=156.1, 140.6, 134.8, 124.7, 84.0, 60.6, 26.0, 25.1, 18.5, −4.4; HR-MS (ESI): calcd. For C$_{20}$H$_{33}$$^{10}$BO$_3$Si (M$^+$): 359.2328; found: 359.2333.

Example 16

Cross Metathesis Reactions

Procedure for Cross Metathesis Reactions in 0.02 M KHSO$_4$ in TPGS-750-M:

tert-Butyl(2-allylphenoxy)dimethylsilane (124 mg, 0.50 mmol), methyl vinyl ketone (106 mg, 1.50 mmol) and Grubbs-2 catalyst (8.5 mg, 0.010 mmol) were sequentially added into a Teflon-coated-stir-bar-containing Biotage 2-5 mL microwave reactor vial at rt, and sealed with a septum. An aliquot of 0.02 M KHSO$_4$ in TPGS-750-M/H$_2$O (1.0 mL; 2.5% TPGS-750-M by weight) was added via syringe, and the resulting solution was allowed to stir at rt for 4 h. The homogeneous reaction mixture was then diluted with EtOAc (2 mL), filtered through a bed of silica gel, and the bed further washed (3×5 mL) with EtOAc to collect all of the cross-coupled material. The volatiles were removed in vacuo to afford the crude product which was subsequently purified by flash chromatography on silica gel (eluting with 3% EtOAc/hexanes) afforded the product as a colorless oil (135 mg, 93%).

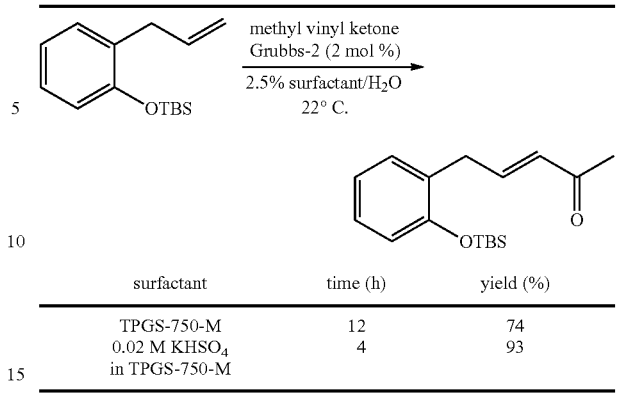

| surfactant | time (h) | yield (%) |
|---|---|---|
| TPGS-750-M | 12 | 74 |
| 0.02 M KHSO$_4$ in TPGS-750-M | 4 | 93 |

Example 17

Heck Coupling Reactions in Aqueous Salt Solutions

Procedure for Heck Coupling in 3 M NaCl in TPGS-750-M:
The catalyst Pd[P(t-Bu)$_3$]$_2$ (5.1 mg, 0.01 mmol) and 3,5-dimethyl bromobenzene (68 μL, 0.50 mmol) were added under argon into a 5.0 mL microwave vial equipped with a large stir bar and Teflon lined septum. An aliquot of 3 M NaCl in TPGS-750-M/H$_2$O (1.0 mL; 5.0% TPGS-750-M by weight) solution, triethylamine (208 μL, 1.50 mmol), and tert-butyl acrylate (145 μL, 1.0 mmol) were added by syringe, and the resulting solution was allowed to stir at rt for 14 h. The homogeneous reaction mixture was then diluted with EtOAc (2 mL), filtered through a bed of silica gel, and the bed further washed (3×5 mL) with EtOAc to collect all of the coupled material. The volatiles were removed in vacuo to afford the crude product which was subsequently purified by flash chromatography on silica gel (eluting with 2% EtOAc/hexanes) afforded the product as a colorless oil (110 mg, 95%).

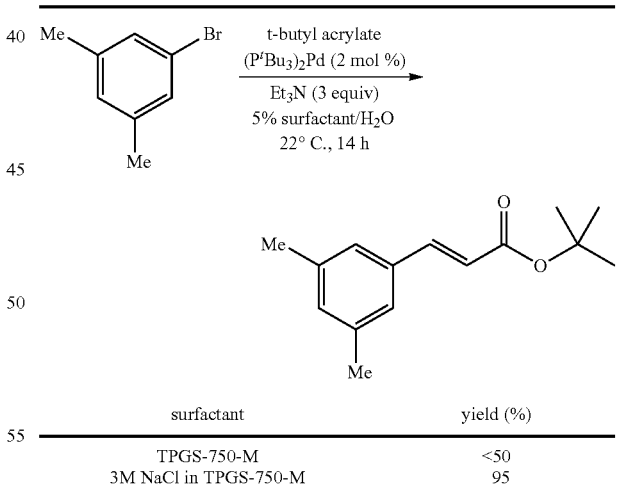

| surfactant | yield (%) |
|---|---|
| TPGS-750-M | <50 |
| 3M NaCl in TPGS-750-M | 95 |

The present application also provides C—H activation and cross-coupling reactions of aryl ureas in water. Such reactions can be carried out using the surfactants disclosed herein, particularly TPGS-M-PEG-750.

The articles "a," "an" and "the" as used herein do not exclude a plural number of the referent, unless context clearly dictates otherwise. The conjunction "or" is not mutually exclusive, unless context clearly dictates otherwise. The term "include" is used to refer to non-exhaustive examples.

All references, publications, patent applications, issued patents, accession records and databases cited herein, including in any appendices, are incorporated by reference in their entirety for all purposes.

I claim:

1. A mixture comprising
   (a) water in an amount of at least 1% wt/wt of the mixture;
   (b) a transition metal catalyst; and
   (c) a solubilizing agent having the formula

wherein Z is a hydrophobic group,
   and $Y^1$-$L^1$- has the formula:

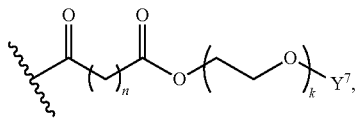

wherein n is an integer selected from 2-10,
   k is 16-20, and $Y^7$ is methyl.

2. The mixture of claim 1, wherein the transition metal catalyst is selected from an organo-palladium or -nickel reagent, organo-copper or -gold reagent, organo-rhodium or -iridium complex, or an organo-ruthenium, -iron, or -osmium reagent, wherein the catalyst is capable of promoting cross-coupling reactions, or other reactions characteristic of catalysis by these metals, that form a carbon-carbon, carbon-heteroatom or carbon-hydrogen bond.

3. The mixture of claim 1, wherein the transition metal catalyst comprises less than 5 mole %, less than 3 mole % or less than 2 mole % of the mixture.

4. The mixture of claim 1, further comprising (i) a coupling substrate and (ii) a coupling partner.

5. The mixture of claim 4, wherein water is the sole solvent.

6. The mixture of claim 5, wherein the coupling substrate is selected from substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl; and wherein the coupling partner is selected from H, substituted or unsubstituted amine, substituted or unsubstituted silane, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl.

7. The mixture of claim 4, wherein the coupling substrate is a substituted or unsubstituted alkene, a substituted or unsubstituted alkyne, a substituted or unsubstituted enyne, a substituted or unsubstituted enone or enoate or a substituted or unsubstituted ynone or ynoate.

8. The mixture of claim 4, wherein the coupling substrate is selected from a substituted or unsubstituted vinyl halide, substituted or unsubstituted vinyl pseudohalide, substituted or unsubstituted allylic alcohol, substituted or unsubstituted allylic ether, substituted or unsubstituted aryl or heteroaryl halide and substituted or unsubstituted aryl or heteroaryl pseudohalide.

9. The mixture of claim 4, wherein the coupling partner is selected from a mono-substituted, disubstituted, trisubstituted, or tetrasubstituted alkene, mono-substituted or disubstituted alkyne, substituted or unsubstituted aryl or heteroaryl halide and substituted or unsubstituted aryl or heteroaryl pseudohalide.

10. The mixture of claim 4, wherein the mixture provides a medium for transition metal-catalyzed cross-coupling reaction comprising olefin cross-metathesis, ring closing metathesis, Sonogashira coupling, Heck coupling, direct amination of free allylic alcohols, aminations of allylic ethers, C—H activation reactions, Suzuki-Miyaura coupling, Buchwald-Hartwig amination, Negishi couplings, benzylic couplings with aryl halides or pseudohalides, silylations of allylic ethers, and aryl-aryl cross-couplings.

11. The mixture of claim 10, wherein the reaction is accelerated by increasing the ionic strength of the reaction medium and/or by the reduction of the pH of the reaction mixture.

12. The mixture of claim 11, wherein increasing the ionic strength is performed by the addition of a metal salt or mixtures of salts, and/or the pH is reduced to a range of pH 2-6.

13. The mixture of claim 1, wherein the hydrophobic group is selected from the group consisting of natural or synthetic alpha-tocopherol, and a ubiquinol moiety.

14. The mixture of claim 1, wherein the hydrophobic group is selected from the group consisting of α-, β-, γ- and Δ-tocopherol.

15. The mixture of claim 14, wherein the hydrophobic group is selected from the group consisting of α-(+)-tocopherol and α-(±)-tocopherol.

* * * * *